United States Patent
Dhingra et al.

(10) Patent No.: US 12,403,146 B2
(45) Date of Patent: Sep. 2, 2025

(54) PREFERRED ORAL TESTOSTERONE UNDECANOATE THERAPY TO ACHIEVE TESTOSTERONE REPLACEMENT TREATMENT

(71) Applicant: Marius Pharmaceuticals, Inc., Raleigh, NC (US)

(72) Inventors: Om Dhingra, Morrisville, NC (US); James S. Bernstein, Raleigh, NC (US)

(73) Assignee: Marius Pharmaceuticals, Inc., Raleigh, NC (US)

( * ) Notice: Subject to any disclaimer, the term of this patent is extended or adjusted under 35 U.S.C. 154(b) by 364 days.

(21) Appl. No.: 17/085,824

(22) Filed: Oct. 30, 2020

(65) Prior Publication Data

US 2022/0265678 A1    Aug. 25, 2022

Related U.S. Application Data

(60) Provisional application No. 62/928,051, filed on Oct. 30, 2019.

(51) Int. Cl.
| | |
|---|---|
| *A61K 31/568* | (2006.01) |
| *A61K 9/00* | (2006.01) |
| *A61K 47/14* | (2017.01) |
| *A61K 47/22* | (2006.01) |
| *A61K 47/44* | (2017.01) |

(52) U.S. Cl.
CPC .......... *A61K 31/568* (2013.01); *A61K 9/0053* (2013.01); *A61K 47/14* (2013.01); *A61K 47/22* (2013.01); *A61K 47/44* (2013.01)

(58) Field of Classification Search
CPC ..... A61K 31/568; A61K 9/0053; A61K 47/14
See application file for complete search history.

(56) References Cited

U.S. PATENT DOCUMENTS

| | | | |
|---|---|---|---|
| 4,147,783 | A | 4/1979 | van der Vies |
| 4,797,625 | A | 1/1989 | Nakazawa |
| 5,376,641 | A | 12/1994 | Ammeraal |
| 5,567,439 | A | 10/1996 | Myers et al. |
| 5,645,856 | A | 7/1997 | Lacy et al. |
| 6,087,353 | A | 7/2000 | Stewart et al. |
| 6,248,363 | B1 | 6/2001 | Patel et al. |
| 6,267,985 | B1 | 7/2001 | Chen et al. |
| 6,284,268 | B1 | 9/2001 | Mishra et al. |
| 6,294,192 | B1 | 9/2001 | Patel et al. |
| 6,309,663 | B1 | 10/2001 | Patel et al. |

(Continued)

FOREIGN PATENT DOCUMENTS

| | | |
|---|---|---|
| CN | 1010538 B | 11/1990 |
| CN | 102083420 A | 6/2011 |

(Continued)

OTHER PUBLICATIONS

"Saw palmetto extract," Wikipedia. < https://en.wikipedia.org/wiki/Saw_palmetto_extract>, retrieved Jun. 27, 2017 (3 pages).

(Continued)

*Primary Examiner* — San Ming R Hui
(74) *Attorney, Agent, or Firm* — Clark & Elbing LLP

(57) ABSTRACT

The present invention features new testosterone undecanoate (TU) dosing regimens, e.g., for testosterone replacement therapy. The TU may be formulated with phytosterols or phytosterol esters.

21 Claims, 8 Drawing Sheets

(56) References Cited

U.S. PATENT DOCUMENTS

| | | |
|---|---|---|
| 6,383,471 B1 | 5/2002 | Chen et al. |
| 6,451,339 B2 | 9/2002 | Patel et al. |
| 6,458,383 B2 | 10/2002 | Chen et al. |
| 6,468,559 B1 | 10/2002 | Chen et al. |
| 6,569,463 B2 | 5/2003 | Patel et al. |
| 6,652,880 B1 | 11/2003 | Aylwin et al. |
| 6,696,484 B2 | 2/2004 | Liao et al. |
| 6,720,001 B2 | 4/2004 | Chen et al. |
| 6,742,448 B1 | 6/2004 | Davis et al. |
| 6,742,488 B2 | 6/2004 | Bonde et al. |
| 6,743,448 B2 | 6/2004 | Kryger |
| 6,761,903 B2 | 7/2004 | Chen et al. |
| 6,838,484 B2 | 1/2005 | Steiner et al. |
| 6,923,988 B2 | 8/2005 | Patel et al. |
| 6,977,083 B1 | 12/2005 | Huebler et al. |
| 6,982,281 B1 | 1/2006 | Chen et al. |
| 7,138,389 B2 | 11/2006 | Amory et al. |
| 7,374,779 B2 | 5/2008 | Chen et al. |
| 8,241,664 B2 | 8/2012 | Dudley et al. |
| 8,492,369 B2 | 7/2013 | Dudley et al. |
| 8,512,794 B2 | 8/2013 | Perlman |
| 8,778,916 B2 | 7/2014 | Dudley et al. |
| 8,828,428 B1 | 9/2014 | Dudley et al. |
| 9,034,858 B2 | 5/2015 | Giliyar et al. |
| 9,205,057 B2 | 12/2015 | Giliyar et al. |
| 9,480,690 B2 | 11/2016 | Giliyar et al. |
| 9,757,390 B2 | 9/2017 | Giliyar et al. |
| 10,576,089 B2 | 3/2020 | Dhingra |
| 10,576,090 B2 | 3/2020 | Dhingra |
| 10,716,794 B2 | 7/2020 | Giliyar et al. |
| 11,179,402 B2 | 11/2021 | Dudley et al. |
| 11,179,403 B2 | 11/2021 | Dudley et al. |
| 11,331,325 B2 | 5/2022 | Dudley et al. |
| 11,590,146 B2 | 2/2023 | Dhingra |
| 11,617,758 B2 | 4/2023 | Dhingra et al. |
| 2002/0012680 A1 | 1/2002 | Patel et al. |
| 2003/0077297 A1 | 4/2003 | Chen et al. |
| 2003/0104048 A1 | 6/2003 | Patel et al. |
| 2003/0203043 A1 | 10/2003 | Yegorova |
| 2003/0236236 A1 | 12/2003 | Chen et al. |
| 2004/0087564 A1 | 5/2004 | Wright et al. |
| 2004/0115287 A1 | 6/2004 | Chen et al. |
| 2004/0127476 A1 | 7/2004 | Kershman et al. |
| 2005/0100608 A1 | 5/2005 | Ebert |
| 2005/0101517 A1 | 5/2005 | De Nijs et al. |
| 2005/0153948 A1 | 7/2005 | Spilburg |
| 2005/0176692 A1 | 8/2005 | Amory et al. |
| 2005/0287203 A1 | 12/2005 | Nijs De et al. |
| 2006/0003002 A1 | 1/2006 | Fikstad et al. |
| 2006/0034937 A1 | 2/2006 | Patel |
| 2006/0263397 A1 | 11/2006 | Li et al. |
| 2007/0009559 A1 | 1/2007 | Li et al. |
| 2007/0022674 A1 | 2/2007 | Worthington |
| 2007/0078091 A1 | 4/2007 | Hubler et al. |
| 2007/0154533 A1 | 7/2007 | Dudley |
| 2007/0190080 A1 | 8/2007 | Friedman |
| 2007/0196440 A1 | 8/2007 | Shulman et al. |
| 2007/0254026 A1 | 11/2007 | Stewart |
| 2008/0124387 A1 | 5/2008 | Spilburg |
| 2008/0200533 A1 | 8/2008 | Krishnan |
| 2008/0206161 A1 | 8/2008 | Tamarkin et al. |
| 2008/0249076 A1 | 10/2008 | Holm et al. |
| 2008/0261937 A1 | 10/2008 | Dudley et al. |
| 2008/0305177 A1 | 12/2008 | Kershman et al. |
| 2008/0317844 A1 | 12/2008 | Dudley et al. |
| 2009/0074859 A1 | 3/2009 | Patel |
| 2009/0075961 A1 | 3/2009 | Ebert |
| 2009/0077961 A1 | 3/2009 | Baker |
| 2009/0123564 A1 | 5/2009 | Jain et al. |
| 2010/0136105 A1 | 6/2010 | Chen et al. |
| 2010/0137271 A1 | 6/2010 | Chen et al. |
| 2010/0173882 A1 | 7/2010 | Giliyar et al. |
| 2011/0142945 A1 | 6/2011 | Chen et al. |
| 2011/0160168 A1 | 6/2011 | Dhingra |
| 2011/0251167 A1 | 10/2011 | Dudley et al. |
| 2011/0263552 A1 | 10/2011 | Dhingra et al. |
| 2011/0312928 A1 | 12/2011 | Nachaegari et al. |
| 2012/0135069 A1 | 5/2012 | Keck et al. |
| 2012/0135074 A1 | 5/2012 | Giliyar et al. |
| 2012/0148675 A1 | 6/2012 | Chickmath et al. |
| 2012/0244215 A1* | 9/2012 | Giliyar ............... A61K 9/4875 424/452 |
| 2012/0309731 A1 | 12/2012 | Dudley et al. |
| 2012/0322780 A1 | 12/2012 | Giliyar et al. |
| 2013/0022674 A1 | 1/2013 | Dudley et al. |
| 2013/0029947 A1 | 1/2013 | Nachaegari et al. |
| 2013/0303495 A1 | 11/2013 | Dhingra et al. |
| 2014/0011780 A1 | 1/2014 | Dhingra |
| 2015/0018324 A1 | 1/2015 | Chickmath et al. |
| 2015/0190406 A1 | 7/2015 | Giliyar et al. |
| 2015/0273067 A1 | 10/2015 | Patel |
| 2016/0166584 A1 | 6/2016 | Patel et al. |
| 2017/0106002 A1 | 4/2017 | Dudley et al. |
| 2018/0021349 A1 | 1/2018 | Dhingra et al. |
| 2018/0153904 A1 | 6/2018 | Giliyar et al. |
| 2018/0221387 A1 | 8/2018 | Patel et al. |
| 2018/0243319 A1 | 8/2018 | Dhingra |
| 2018/0333422 A1 | 11/2018 | Chidambaram et al. |
| 2019/0070196 A1 | 3/2019 | Dudley et al. |
| 2019/0240236 A1 | 8/2019 | Chidambaram et al. |
| 2019/0321374 A1 | 10/2019 | Patel et al. |
| 2019/0350942 A1 | 11/2019 | Patel et al. |
| 2019/0365780 A1 | 12/2019 | Giliyar et al. |
| 2020/0022991 A1 | 1/2020 | Patel et al. |
| 2020/0046733 A1 | 2/2020 | Dudley et al. |
| 2020/0061191 A1 | 2/2020 | Patel |
| 2020/0069805 A1 | 3/2020 | Fikstad et al. |
| 2020/0093836 A1 | 3/2020 | Dudley et al. |
| 2020/0155570 A1 | 5/2020 | Patel et al. |
| 2020/0188304 A1 | 6/2020 | Chickmath et al. |
| 2020/0197412 A1 | 6/2020 | Dudley et al. |
| 2020/0222425 A1 | 7/2020 | Patel et al. |
| 2020/0282061 A1 | 9/2020 | Chen et al. |
| 2020/0323880 A1 | 10/2020 | Dudley et al. |
| 2020/0383997 A1 | 12/2020 | Giliyar et al. |
| 2020/0383998 A1 | 12/2020 | Patel et al. |
| 2020/0383999 A1 | 12/2020 | Giliyar et al. |
| 2020/0390784 A1 | 12/2020 | Dhingra |
| 2020/0390785 A1 | 12/2020 | Patel et al. |
| 2021/0007978 A1 | 1/2021 | Patel et al. |
| 2021/0008212 A1 | 1/2021 | Patel |
| 2021/0038615 A1 | 2/2021 | Giliyar et al. |
| 2021/0046087 A1 | 2/2021 | Dhingra et al. |
| 2021/0052604 A1 | 2/2021 | Giliyar et al. |
| 2021/0169899 A1 | 6/2021 | Patel et al. |
| 2021/0177865 A1 | 6/2021 | Giliyar et al. |
| 2023/0398128 A1 | 12/2023 | Dhingra et al. |
| 2024/0000798 A1 | 1/2024 | Dhingra |
| 2024/0342194 A1 | 10/2024 | Dhingra et al. |

FOREIGN PATENT DOCUMENTS

| | | | |
|---|---|---|---|
| EP | 1925294 A1 | 5/2008 | |
| EP | 2519230 A2 * | 11/2012 | ........... A61K 31/473 |
| EP | 2682111 A1 | 1/2014 | |
| EP | 2979699 A1 | 2/2016 | |
| EP | 2985026 A1 | 2/2016 | |
| EP | 3078368 A1 | 10/2016 | |
| JP | 2008-133281 A | 6/2008 | |
| WO | WO-95/24893 | 9/1995 | |
| WO | WO-97/40823 A1 | 11/1997 | |
| WO | WO-99/59556 A1 | 11/1999 | |
| WO | WO-03/010146 A1 | 2/2003 | |
| WO | WO-03/094891 A1 | 11/2003 | |
| WO | WO-2005/051290 A2 | 6/2005 | |
| WO | WO-2006/084312 A1 | 8/2006 | |
| WO | WO-2006/113505 A2 | 10/2006 | |
| WO | WO-2010/081032 A2 | 7/2010 | |
| WO | WO-2011/082384 A2 | 7/2011 | |
| WO | WO-2011129812 A1 * | 10/2011 | ........... A61K 31/568 |
| WO | WO-2012/092202 A2 | 7/2012 | |
| WO | WO-2014/096139 A1 | 6/2014 | |
| WO | WO-2014/143127 A1 | 9/2014 | |
| WO | WO-2015/193224 A1 | 12/2015 | |

(56) References Cited

FOREIGN PATENT DOCUMENTS

| | | |
|---|---|---|
| WO | WO-2018/098501 A1 | 5/2018 |
| WO | WO-2020/018974 A1 | 1/2020 |
| WO | WO-2020/065401 A1 | 4/2020 |
| WO | WO-2021/168573 A1 | 9/2021 |
| WO | WO-2022/245933 A1 | 11/2022 |

OTHER PUBLICATIONS

"SOV Therapeutics Receives U.S. Orphan Drug Designation for the Use of Oral Testosterone Undecanoate in the Treatment of Constitutional Delay in Growth and Puberty in Adolescent Boys (14-17 Years of Age)," http://biospace.com/News/sov-therapeutics-receives-u-s-orphan-drug/288181, retrieved Jul. 26, 2017 (1 page).

"Technical Data Sheet," CardioAid XF Plant Sterols ADM, Product Code 040551 (2 pages).

Abidi, "Chromatographic analysis of plant sterols in foods and vegetable oils," J Chromatogr A. 935(1-2):173-201 (2001).

Advertisement for Eli Lilly and Company, "Cytellin sitosterols: the cholesterol-lowering agent with an unparalleled record of safety," Bull NY Acad Med. 39(8) (1963) (2 pages).

Advisory Action for U.S. Appl. No. 12/983,216, mailed Apr. 25, 2013 (3 pages).

Advisory Action for U.S. Appl. No. 12/983,216, mailed Mar. 21, 2013 (3 pages).

Amory et al., "Oral testosterone in oil plus dutasteride in men: a pharmacokinetic study," J Clin Endocrinol Metab. 90(5):2610-7 (2005).

Amory et al., "Oral testosterone in oil: pharmacokinetic effects of 5alpha reduction by finasteride or dutasteride and food intake in men," J Androl. 27(1):72-8 (2006).

Amory et al., "Oral testosterone with and without concomitant inhibition of 5alpha-reductase by dutasteride in hypogonadal men for 28 days," J Urology. 185:626-32 (2011).

Andriole et al., "Effect of dutasteride on the risk of prostate cancer," Ne J Med. 362(13):1192-202 (2010).

Araya et al., "The novel formulation design of O/W microemulsion for improving the gastrointestinal absorption of poorly water soluble compounds," Int J Pharm. 305(1-2):61-74 (2005).

Armand et al., "Digestion and absorption of 2 fat emulsions with different droplet sizes in the human digestive tract," Am J Clin Nutr. 70(6):1096-106 (1999).

Awad et al., "Phytosterol feeding induces alteration in testosterone metabolism in rat tissues," J Nutr Biochem 9(12):712-7 (1998).

Bagchus et al., "Important effect of food on the bioavailability of oral testosterone undecanoate," Pharmacotherapy. 23(3):319-25 (2003).

BASF, "DL-alpha-Tocopherol: Technical information human nutrition." (2009, 2 pages).

Bhasin et al., "Drug insight: Testosterone and selective androgen receptor modulators as anabolic therapies for chronic illness and aging," available in PMC Nov. 9, 2007, published in final edited form as: Nat Clin Pract Endrocrinol Metab. 2(3):146-59 (2006) (20 pages).

Bollman et al., "Techniques for the collection of lymph from the liver, small intestine, or thoracic duct of the rat," J Lab Clin Med. 33(10):1349-52 (1948).

Borgström et al., "Studies of intestinal digestion and absorption in the human," J Clin Invest. 36(10):1521-36 (1957).

Borowy-Borowski et al., "Unique technology for solubilization and delivery of highly lipophilic bioactive molecules," J Drug Target. 12(7):415-24 (2004).

Borst et al., "Inhibition of 5alpha-reductase blocks prostate effects of testosterone without blocking anabolic effects," Am J Physiol Endocrinol Metab. 288:E222-7 (2005).

Bramson et al., "Unique preclinical characteristics of GG745, a potent dual inhibitor of 5AR," J Pharmacol Exp Ther. 282(3) 1496-502 (1997).

Briefing Document for Bone, Reproductive, and Urologic Drugs Advisory Committee, "Oral Testosterone Undecanoate Capsules (Jatenzo™) for Testosterone Replacement Therapy in Hypogonadal Men," Clarus Therapeutics, Inc., dated Jan. 9, 2018 (116 pages).

Brown et al., "Plant sterol and stanol substrate specificity of pancreatic cholesterol esterase," J. Nutr. Bioch. 21(8):736-40 (2010).

Cabeza et al., "Effects of beta-sitosterol as Inhibitor of 5alpha-reductase in Hamster Prostate," Proc West Pharmacol Soc. 46:153-5 (2003).

Carey et al., "The characteristics of mixed micellar solutions with particular reference to bile," Am J Med. 49(5):590-608 (1970). Abstract only.

Carlin et al., "Disposition and pharmacokinetics of [14C]finasteride after oral administration in humans," Drug Metab Dispos. 20(2):148-55 (1992).

Charman et al., "Physicochemical and physiological mechanisms for the effects of food on drug absorption: the role of lipids and pH," J Pharm Sci. 86(3):269-282 (1997).

Chen et al., "Blockade of Androgen Markers Using a Novel Betasitosterol, Thioctic Acid and Carnitine-containing Compound in Prostate and Hair Follicle Cell-based Assays," Phytother Res. 30(6):1016-20 (2016).

Coert et al., "The pharmacology and metabolism of testosterone undecanoate (TU), a new orally active androgen," Acta Endocrinol (Copenh). 79(4):789-800 (1975).

Communication pursuant to Article 94(3) EPC and Form 2906 for European Patent Application No. 13877592.9, dated Jun. 16, 2017 (5 pages).

Communication pursuant to Article 94(3) EPC for European Application No. 13170663.2, dated Oct. 7, 2016 (5 pages).

Compound Summary for CID 14985: Vitamin E, https://pubchem.ncbi.nlm.nih.gov/compound/alpha-Tocopherol, retrieved May 22, 2018 (106 pages).

Connors et al., "Using a Portfolio of Particle Growth Technologies to Enable Delivery of Drugs with Poor Water Solubility," Drug Deliv Tech. 4(8):1-11 (2004).

Corona et al., "Update in testosterone therapy for men," J Sex Med. 8(3):639-54 (2011).

Daggett et al., "Oral testosterone, a reappraisal," Horm Res. 9(3):121-9 (1978).

Debruyne et al., "Efficacy and safety of long-term treatment with the dual 5 alpha-reductase inhibitor dutasteride in men with symptomatic benign prostatic hyperplasia," Eur Urol. 46:488-95 (2004).

Decision to refuse a European Patent application for European Patent Application No. 13170663.2, dated May 7, 2018 (10 pages).

Delaney et al., "Oral absorption of phytosterols and emulsified phytosterols by Sprague-Dawley rats," J Nutr Biochem. 15(5):289-95 (2004).

Diver et al., "Diurnal rhythms of serum total, free and bioavailable testosterone and of SHBG in middle-aged men compared with those in young men," Clin Endocrinol. 58(6):710-7 (2003).

Eldridge et al., "Controlled vaccine release in the gut-associated lymphoid tissues. I. Orally administered biodegradable microspheres target the peyer's patches," J Control Release. 11(1-3):205-14 (1990) (Abstract only).

Extended European Search Report for European Patent Application No. 10841783.3, dated Jun. 7, 2013 (8 pages).

Extended European Search Report for European Patent Application No. 13170663.2, dated Dec. 10, 2013 (8 pages).

Extended European Search Report for European Patent Application No. 13877592.9, dated Sep. 8, 2016 (6 pages).

First Examination Report for Indian Patent Application No. 1959/KOLNP/2012, dated May 31, 2018 (7 pages).

First Examination Report for New Zealand Patent Application No. 631833, mailed Nov. 6, 2015 (2 pages).

First Office Action for Chinese Patent Application No. 201380074669.9, dated Mar. 22, 2017 (23 pages).

Fogh et al., "Serum-testosterone during oral administration of testosterone in hypogonadal men and transsexual women," Acta Endocrinol (Copenh). 87(3):643-9 (1978).

Food and Drug Administration, "Federal Register" 75(235):76526-71 (2010).

Gerbino. *Remington: the science and practice of pharmacy*. 21st edition. Lippincott Williams & Wilkins, 2006. Summary only.

(56) References Cited

OTHER PUBLICATIONS

Giliyar et al., "Challenges & Opportunities in Oral Delivery of Poorly Water-Soluble Drugs," Drug Deliv Tech. 6(1):57-63 (2006).
Grosso et al., "Fatty acid, sterol and proximate compositions of peanut species (*Arachis* L.) seeds from Bolivia and Argentina," Grasas y Aceites. 48(4):219-25 (1997).
Gursoy et al., "Self-emulsifying drug delivery systems (SEDDS) for improved oral delivery of lipophilic drugs," Biomed Pharmacother. 58(3):173-82 (2004).
Haren et al., "Effect of 12 month oral testosterone on testosterone deficiency symptoms in symptomatic elderly males with low-normal gonadal status," Age Ageing. 34:125-30 (2005).
Hawley et al., "Targeting of colloids to lymph nodes: influence of lymphatic physiology of colloidal characteristics," Adv Drug Deliv Reviews. 17(1):129-48 (1995).
Heinemann et al., "Effect of low-dose sitostanol on serum cholesterol in patients with hypercholesterolemia," Atherosclerosis. 61(3):219-23 (1986) (Abstract only).
Horst et al., "Lymphatic absorption and metabolism of orally administered testosterone undecanoate in man," Klin Wochenschr. 54:875-9 (1976).
Houwing et al., "Pharmacokinetic study in women of three different doses of a new formulation of oral testosterone undecanoate, Andriol Testocaps," Pharmacotherapy. 23(10):1257-65 (2003).
International Search Report and Written Opinion for International Patent Application No. PCT/US2013/049405, mailed Dec. 12, 2013 (15 pages).
Itoh et al., "Sterol composition of 19 vegetable oils," J Am Oil Chem Soc. 50:122-5 (1973).
Johnsen et al., "Therapeutic effectiveness of oral testosterone," Lancet. 2:1473-5 (1974).
Johnsen, "Long-term oral testosterone and liver function," Lancet. 311(8054):50 (1978).
Kaukonen et al., "Drug solubilization behavior during in vitro digestion of simple triglyceride lipid solution formulations," Pharm Res. 21(2):245-53 (2004).
Kincl et al., "Increasing intestinal absorption of drugs by formulation," Arch Pharm (Weinheim). 319(7):615-24 (1986).
Kossena et al., "Influence of the intermediate digestion phases of common formulation lipids on the absorption of a poorly water-soluble drug," J Pharm Sci. 94(3):481-92 (2005).
Kossena et al., "Probing drug solubilization patterns in the gastrointestinal tract after administration of lipid-based delivery systems: a phase diagram approach," J Pharm Sci. 93(2):332-48 (2004).
Kovarik et al., "Reduced inter-and intraindividual variability in cyclosporine pharmacokinetics from a microemulsion formulation," J Pharm Sci. 83(3):444-6 (1994).
Kwei et al., "Lymphatic uptake of MK-386, a sterol 5alpha-reductase inhibitor, from aqueous and lipid formulations," Int J Pharm. 164(1-2):37-44 (1998).
Lea et al., "Safety evaluation of phytosterol-esters. Part 9: Results of a European post-launch monitoring programme," Food and Chem Toxicol. 44:1213-22 (2006).
Lees et al., "Plant sterols as cholesterol-lowering agents: clinical trials in patients with hypercholesterolemia and studies of sterol balance," Atherosclerosis. 28(3):325-338 (1977) (Abstract only).
Macgregor et al., "Influence of lipolysis on drug absorption from the gastro-intestinal tract," Adv Drug Deliv Rev. 25(1):33-46 (1997).
Marks et al., "Long-term effects of finasteride on prostate tissue composition," Urology. 53(3):574-80 (1999).
Matsumoto, "Hormonal therapy of male hypogonadism," Endocrinol Metab Clin North Am. 23(4):857-75 (1994).
Mattson et al., "Optimizing the effect of plant sterols on cholesterol absorption in man," Am J Clin Nutr. 35:697-700 (1982).
Mazer et al., "Enhanced transdermal delivery of testosterone: a new physiological approach for androgen replacement in hypogonadal men," J Control Release. 19:347-62 (1992).
McConnell et al., "The effect of finasteride on the risk of acute urinary retention and the need for surgical treatment among men with benign prostatic hyperplasia. Finasteride Long-Term Efficacy and Safety Study Group," N Engl J Med. 338(9):557-63 (1998).
Melander, "Influence of food and different nutrients on drug bioavailability," World Rev Nutr Diet. 43:34-44 (1984).
Merck Canada Inc. "Andriol Product Monograph: Part III: Consumer Information." https://pdf.hres.ca/dpd_pm/00033378.PDF (2015) (3 pages).
Micallef et al., "The lipid-lowering effects of phytosterols and (n-3) polyunsaturated fatty acids are synergistic and complementary in hyperlipidemic men and women," J Nutr. 138(6):1086-90 (2008).
Miettinen et al., "Reduction of serum cholesterol with sitostanol-ester margarine in a mildly hypercholesterolemic population," N Engl J Med. 333(20)1308-12 (1995).
Miettinen et al., "Serum plant sterols and cholesterol precursors reflect cholesterol absorption and synthesis in volunteers of a randomly selected male population," Am J Epidemiol. 131(1):20-31 (1990). Abstract only.
Mostaghel et al., "Intraprostatic androgens and androgen-regulated gene expression persist after testosterone suppression: therapeutic implications for castration-resistant prostate cancer," Cancer Res. 67(10):5033-41 (2007).
Mueller et al., "Influence of a fat-rich meal on the pharmacokinetics of a new oral formulation of cyclosporine in a crossover comparison with the market formulation," Pharm Res. 11(1):151-5 (1994).
Nieschlag et al., "Influence of sex, testicular development and liver function on the bioavailability of oral testosterone," Eur J Clin Invest. 7:145-7 (1977).
Nieschlag et al., "Plasma androgen levels in men after oral administration of testosterone or testosterone undecanoate," Acta Endocrinol (Copenh). 79:366-74 (1975).
Nishiyama et al., "The influence of androgen deprivation therapy on dihydrotestosterone levels in the prostatic tissue of patients with prostate cancer," Clin Cancer Res. 10:7121-6 (2004).
Office Action for Canadian Patent Application No. 2,822,435, mailed Sep. 6, 2016 (4 pages).
Office Action for Chinese Patent Application No. 201380074669.9 and English Translation dated Jan. 19, 2018 (17 pages).
Office Action for European Patent Application No. 10841783.3, dated Nov. 26, 2015 (5 pages).
Office Action for Japanese Patent Application No. 2012-547323, mailed Nov. 18, 2014 (8 pages).
Office Action for Japanese Patent Application No. 2012-547323, mailed Sep. 17, 2015 (5 pages).
Office Action for Japanese Patent Application No. 2013-124891, mailed Dec. 12, 2014 (9 pages).
Office Action for U.S. Appl. No. 12/983,216, mailed Jan. 4, 2013 (20 pages).
Office Action for U.S. Appl. No. 13/174,756, mailed Mar. 14, 2013 (29 pages).
Office Action for U.S. Appl. No. 13/843,223, mailed Mar. 31, 2014 (22 pages).
Office Action for U.S. Appl. No. 13/843,223, mailed Apr. 1, 2016 (25 pages).
Office Action for U.S. Appl. No. 13/843,223, mailed Aug. 28, 2015 (31 pages).
Office Action for U.S. Appl. No. 13/843,223, mailed Oct. 14, 2016 (26 pages).
Office Action for U.S. Appl. No. 13/843,223, mailed Oct. 23, 2014 (24 pages).
Office Action for U.S. Appl. No. 12/983,216, mailed Apr. 27, 2016 (25 pages).
Office Action for U.S. Appl. No. 12/983,216, mailed Aug. 1, 2012 (14 pages).
Office Action for U.S. Appl. No. 12/983,216, mailed Jan. 22, 2015 (31 pages).
Office Action for U.S. Appl. No. 12/983,216, mailed Jul. 29, 2013 (37 pages).
Office Action for U.S. Appl. No. 12/983,216, mailed Jun. 7, 2012 (12 pages).
Office Action for U.S. Appl. No. 12/983,216, mailed Mar. 7, 2014 (43 pages).
Office Action for U.S. Appl. No. 12/983,216, mailed Sep. 2, 2015 (22 pages).

(56) References Cited

OTHER PUBLICATIONS

Office Action for U.S. Appl. No. 13/174,756, mailed Oct. 2, 2013 (19 pages).
Office Action for U.S. Appl. No. 13/936,036, mailed Dec. 5, 2014 (13 pages).
Office Action for U.S. Appl. No. 13/936,036, mailed Feb. 17, 2016 (13 pages).
Office Action for U.S. Appl. No. 13/936,036, mailed Jul. 30, 2015 (11 pages).
Office Action for U.S. Appl. No. 13/936,036, mailed Jun. 5, 2014 (10 pages).
Office Action for U.S. Appl. No. 13/936,036, mailed Sep. 6, 2016 (22 pages).
Office Action Summary and Notice of References Cited for U.S. Appl. No. 13/936,036, dated Jun. 18, 2018 (21 pages).
Office Action Summary and Notice of References Cited for U.S. Appl. No. 15/959,626, dated Jul. 20, 2018 (28 pages).
Page et al., "Dihydrotestosterone administration does not increase intraprostatic androgen concentrations or alter prostate androgen action in healthy men: a randomized-controlled trial," J Clin Endocrinol Metab. 96(2):430-7 (2011).
Page et al., "Persistent intraprostatic androgen concentrations after medical castration in healthy men," J Clin Endocrinol Metab. 91(10):3850-6 (2006).
Pedersen et al., "A comparison of the solubility of danazol in human and simulated gastrointestinal fluids," Pharm Res. 17(7):891-4 (2000).
Perlman et al., "Development of a self-emulsifying formulation that reduces the food effect for torcetrapib," Int J Pharm. 351(1-2):15-22 (2008).
Phillips et al., "Free and Esterified Sterol Composition of Edible Oils and Fats," J Food Composition and Analysis. 15:123-42 (2002).
Porter et al., "Intestinal lymphatic drug transport: an update," Adv Drug Deliv Reviews. 50:61-80 (2001).
Porter et al., "Lipids and lipid-based formulations: optimizing the oral delivery of lipophilic drugs," Nat Rev Drug Discov. 6(3):231-48 (2007).
Porter et al., "Uptake of drugs into the intestinal lymphatics after oral administration," Adv Drug Deliv Reviews. 25:71-89 (1997).
Pouton, "Formulation of poorly water-soluble drugs for oral administration: physicochemical and physiological issues and the lipid formulation classification system," Eur J Pharm Sci. 29(3-4):278-87 (2006).
Pouton, "Formulation of self-emulsifying drug delivery systems," Adv Drug Deliv Rev. 25(1):47-58 (1997).
Prager et al., "A Randomized, Double-Blind, Placebo-Controlled Trial to Determine the Effectiveness of Botanically Derived Inhibitors of 5-alpha-Reductase in the Treatment of Androgenetic Alopecia," J Altern Complem Med. 8(2):143-52 (2002).
PubChem CID 14870. Retrieved on Jun. 28, 2018 (21 pages).
Reininger et al., "Effect of digestion on distribution of blood flow in the rat," Science. 126(3284):1176 (1957).
Right fax interview agenda concerning U.S. Appl. No. 13/012,084, dated Aug. 16, 2013 (9 pages).
Roehrborn et al., "Efficacy and safety of a dual inhibitor of 5-alpha-reductase types 1 and 2 (dutasteride) in men with benign prostatic hyperplasia," Urology. 60(3):434-41 (2002).
Roth et al., "Steady-state pharmacokinetics of oral testosterone undecanoate with concomitant inhibition of 5alpha-reductase by finasteride," Int J Androl. 34(6:1):541-7 (2011).
Russell et al., "Steroid 5 alpha-reductase: two genes/two enzymes," Annu Rev Biochem. 63:25-61 (1994).
Schnabel et al., "The effect of food composition on serum testosterone levels after oral administration of Andriol Testocaps," Clin Endocrinol (Oxf.). 66:579-85 (2007).
Search Report for Taiwanese Patent Application No. 103109505, completed Aug. 7, 2017 (2 pages).
Shackleford et al., "Contribution of lymphatically transported testosterone undecanoate to the systemic exposure of testosterone after oral administration of two andriol formulations in conscious lymph duct-cannulated dogs," J Pharmacol Exp Ther. 306(3):925-33 (2003).
Shah et al., "Self-emulsifying drug delivery systems (SEDDS) with polyglycolyzed glycerides for improving in vitro dissolution and oral absorption of lipophilic drugs," Int J Pharm. 106:15-23 (1994).
Sheen et al., "Bioavailability of a poorly water-soluble drug from tablet and solid dispersion in humans," J Pharm Sci. 80(7):712-4 (1991).
Sikorska et al., "Derivatised alpha-tocopherol as a CoQ10 carrier in a novel water-soluble formulation," BioFactors. 18:173-83 (2003).
Steiner, "Clinical pharmacokinetics and pharmacodynamics of finasteride," Clin Pharmacokinet. 30(1):16-27 (1996). Abstract Only.
Täuber et al., "Absolute bioavailability of testosterone after oral administration of testosterone-undecanoate and testosterone," Eur J Drug Metab Pharmacokinet. 11(2):145-9 (1986).
Technical Data Sheet for CardioAid XF—Plant Sterols—040551, Archer Daniels Midland Company, dated Apr. 10, 2019 (1 page).
Tilvis et al., "Serum plant sterols and their relation to cholesterol absorption," Am J Clin Nutr. 43:92-7 (1986).
Traish et al., "Adverse side effects of 5alpha-reductase inhibitors therapy: persistent diminished libido and erectile dysfunction and depression in a subset of patients," J Sex Med. 8(3):872-84 (2011).
Trevaskis et al., "Bile increases intestinal lymphatic drug transport in the fasted rat," Pharm Res. 22(11):1863-70 (2005).
Trevaskis et al., "Lipid-based delivery systems and intestinal lymphatic drug transport," Adv Drug Deliv Rev. 60:702-716 (2008).
Trevaskis et al., "The lymph lipid precursor pool is a key determinant of intestinal lymphatic drug transport," J Pharmacol Exp Ther. 316(2):881-91 (2006).
Trevaskis et al., "The role of the intestinal lymphatics in the absorption of two highly lipophilic cholesterol ester transfer protein inhibitors (CP524,515 and CP532,623)," Pharm Res. 27(5):878-93 (2010).
U.S. Appl. No. 15/959,626, filed Apr. 23, 2018 (87 pages).
Unpublished U.S. Appl. No. 13/843,223, filed Mar. 15, 2013.
Unpublished U.S. Appl. No. 61/291,769, filed Dec. 31, 2009.
Vahouny et al., "Comparative lymphatic absorption of sitosterol, stigmasterol, and fucosterol and differential inhibition of cholesterol absorption," Amer J Clin Nutr. 37(5):805-9 (1983).
Von Eckardstein et al., "Treatment of male hypogonadism with testosterone undecanoate injected at extended intervals of 12 weeks: a phase II study," J Androl. 23(3):419-25 (2002).
Wagner, "Drug bioavailability studies," Hosp Prac. 12:119-27 (1977).
Walsh, "Chemoprevention of prostate cancer," N Engl J Med. 362(13):1237-8 (2010).
Welling, "Effects of food on drug absorption," Pharmacol Ther. 43(3):425-41 (1989).
Welling, "How food and fluid affect drug absorption: results of initial studies," Postgrad Med. 62(1):73-75, 78-82 (1977).
Welling, "Interactions affecting drug absorption," Clin Pharmacokinet. 9:404-34 (1984).
Whitten et al., "Select patients with hypogonadotropic hypogonadism may respond to treatment with clomiphene citrate," Fertil Steril. 86(6):1664-8 (2006).
Yin et al., "Reexamination of pharmacokinetics of oral testosterone undecanoate in hypogonadal men with a new self-emulsifying formulation," available in PMC Sep. 19, 2014, published in final edited form as: J Androl. 33(2):190-201 (2012) (19 pages).
Zmuda et al., "The effect of testosterone aromatization on high-density lipoprotein cholesterol level and postheparin lipolytic activity," Metabolism. 42(4):446-50 (1993).
International Search Report and Written Opinion for International Application No. PCT/US2022/029819, mailed Jul. 28, 2022 (10 pages).
Lachance et al., "Importance of measuring testosterone in enzyme-inhibited plasma for oral testosterone undecanoate androgen replacement therapy clinical trials," Future Sci OA. 1(4):FSO55 (Nov. 1, 2015) (10 pages).
U.S. Appl. No. 63/378,291, Dhingra et al.
Azizi et al., "Phytochemicals With Anti 5-alpha-reductase Activity: A Prospective For Prostate Cancer Treatment," F1000Res. 10:221 (2021) (21 pages).

(56) References Cited

OTHER PUBLICATIONS

Quallich, "Determining when men need testosterone," Clinical Advisor, Jul. 6, 2009 (6 pages).

White et al., "Effects of Oral Testosterone Undecanoate (Kyzatrex) Versus Testosterone Gel (Androgel) on Long-Term (to 12 Months) Blood Pressure Levels," Androgens: Clinical Research and Therapeutics 3.1:233-41 (2022).

White et al., "Effects of the oral testosterone undecanoate Kyzatrex™ on ambulatory blood pressure in hypogonadal men," J Clin Hypertens. 23(7):1420-30 (Jul. 2021).

Swerdloff et al., "A New Oral Testosterone Undecanoate Formulation Restores Testosterone to Normal Concentrations in Hypogonadal Men," J Clin Endocrinol Metab. 105(8):1-17 (Aug. 2020).

Broderick, "FDA accepts application for novel testosterone replacement therapy for hypogonadism," Urology Times. <https://www.urologytimes.com/view/fda-accepts-application-for-novel-trt-for-hypogonadism>, Mar. 11, 2021 (3 pages).

Park, "Kyzatrex Under Review for Primary and Secondary Male Hypogonadism," Medical Professionals Reference. <https://www.biospace.com/marius-pharmaceuticals-submits-new-drug-application-tou-s-fda-for-next-generation-oral-testosterone-replacement-therapy-in-male-patients-with-hypogonadism>, Mar. 11, 2021 (1 page).

"Ambulatory Blood Pressure Monitoring (ABPM) Extension Study of Oral Testosterone Undecanoate in Hypogonadal Men," ClinicalTrials.gov. <https://clinicaltrials.gov/study/NCT04467697?tab=history&a=3#version-content-panel>, Jan. 15, 2021 (7 pages).

Lewington et al., "Age-specific relevance of usual blood pressure to vascular mortality: a meta-analysis of individual data for one million adults in 61 prospective studies," The Lancet 360:1903-13 (Dec. 2002).

"FDA issues class-wide labeling changes for testosterone products", U.S. Food and Drug Administration, <https://www.fda.gov/drugs/drug-safety-and-availability/fda-issues-class-wide-labeling-changes-testosterone-products>, retrieved on Mar. 31, 2025 (2 pages).

Bone, Reproductive, And Urologic Drugs Advisory Committee (BRUDAC) Meeting, U.S. Food and Drug Administration, Jan. 9, 2018, Hyattsville, Maryland (363 pages).

U.S. Appl. No. 18/201,498, Dhingra et al.

U.S. Appl. No. 18/102,136, Dhingra, Om.

U.S. Appl. No. 18/176,166, Dhingra et al.

\* cited by examiner

PREFERRED ORAL TESTOSTERONE UNDECANOATE THERAPY TO ACHIEVE TESTOSTERONE REPLACEMENT TREATMENT

BACKGROUND OF THE INVENTION

For testosterone replacement therapy (TRT) in hypogonadal men, the FDA has imposed regulatory guidelines on testosterone (T) formulations to balance the benefits and safety risks associated with abnormally high T concentrations (see, e.g., page 13 of *Testosterone Replacement Therapy Advisory Committee Briefing Document*, Sep. 17, 2014). These regulatory guidelines include an average T blood serum concentrations (Cavg) in the normal range of 300 to 1000 ng/dL in 75% of subjects, maximum T blood serum concentrations (Cmax) less than 1500 ng/dL in 85% of subjects, not more than 5% between 1800 and 2500 ng/dL, and none above 2500 ng/dL. These guidelines are the standards used to achieve FDA approval to which all pharmaceutical companies attempting to bring testosterone replacement therapies to the market focus their research. To better manage the benefits and safety risks, it is important that formulations and dosing strategies be designed to achieve favorable pharmacokinetic (PK) performance of testosterone or a testosterone prodrug, such as testosterone undecanoate (TU). Accordingly, new formulations, dosage regimens, and titration schemes are needed to meet these standards and improve therapeutic efficacy.

SUMMARY OF THE INVENTION

The present invention features new testosterone undecanoate dosing strategies that include performing plasma or serum measurements of testosterone and titrating the daily dosage up or down, if necessary, in order to achieve favorable PK parameters.

In one aspect, the invention features a method of treating testosterone deficiency in a subject in need thereof. The subject to be treated is a male, e.g., a hypogonadal male. The method includes performing a treatment regimen that includes administering to the subject a pharmaceutical composition including testosterone undecanoate (TU), a non-sterol solubilizing agent effective for solubilization of the TU, and a phytosterol or phytosterol ester. About 400 mg TU may be administered, e.g., at the onset of the treatment regimen. The method may include establishing a first steady state serum concentration of testosterone. The method may include providing a first Serum Value of testosterone in the subject following administration of the TU. Additionally, the method may further include performing a first titration of the testosterone undecanoate, e.g., if necessary. If the first Serum Value of testosterone is less than about 400/F or 400/F+b ng/dL (e.g., a serum concentration of less than about 449 ng/dL or less than about 460 ng/dL or a plasma concentration of less than about 400 ng/dL), then the daily dosage may be increased, e.g., to about 600 mg TU. F corresponds to a predetermined empirical factor that relates the plasma and serum concentrations and is described in more detail below. This may establish a second steady state Serum Value of testosterone that is higher than the first steady state Serum Value of testosterone. If the first Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the daily dosage may be maintained. This may maintain the first steady state Serum Value of testosterone. If the first Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the daily dosage may be decreased, e.g., to about 200 mg TU. This may establish a second steady state Serum Value of testosterone that is lower than the first steady state Serum Value of testosterone.

The Serum Value of testosterone may be measured from about 3 hours to about 6 hours (e.g., 3 hours, 4 hours, 5 hours, or 6 hours, e.g., from about 3 hours to about 5 hours) after administration. The Serum Value of testosterone may be measured from about 3 hours to about 5 hours after administration. The pharmaceutical composition may be administered with a meal. The pharmaceutical composition may be administered in two or more doses (e.g., 2, 3, 4, 5, 6, 7, 8, 9, 10, or more) doses. The pharmaceutical composition may be administered in two doses per day (e.g., twice daily administration). The pharmaceutical composition may be administered in three doses per day. A first dose may be administered in the morning, and a second dose may be administered in the evening. The first dose may include about 200 mg TU, and the second dose may include about 200 mg TU.

In some embodiments, following the first titration: the daily dosage may be increased to about 600 mg TU, and the first dose includes about 300 mg TU, and the second dose includes about 300 mg TU; the daily dosage may be maintained at about 400 mg TU, and the first dose includes about 200 mg TU, and the second dose includes about 200 mg TU; or the daily dosage may be decreased to about 200 mg TU, and the first dose includes about 100 mg TU, and the second dose includes about 100 mg TU.

In some embodiments, a second Serum Value of testosterone may be measured.

In some embodiments, a second titration may be performed, e.g., following the second Serum Value of testosterone measurement.

The first Serum Value of testosterone may be less than about 400/F ng/dL or 400/F+b ng/dL (e.g., a serum concentration of less than about 449 ng/dL or less than about 460 ng/dL or a plasma concentration of less than about 400 ng/dL) and the daily dosage may be increased to about 600 mg TU. This may establish a third steady state Serum Value of testosterone that is higher than the second steady state Serum Value of testosterone. The first Serum Value of testosterone may be from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL) and the dosage may be maintained. This may maintain the second steady state Serum Value of testosterone. The first Serum Value of testosterone may be greater than about 900/F ng/dL or 900/F+b ng/dL (e.g., a serum concentration of greater than about 1011 ng/dL or greater than about 971 ng/dL or a plasma concentration of greater than about 900 ng/dL) and the dosage may be decreased to about 200 mg TU. This may establish a third steady state Serum Value of testosterone that is lower than the first steady state Serum Value of testosterone.

Following the first titration, about 600 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 800 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 600 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 400 mg TU daily to the subject to establish a third steady state Serum Value of testosterone that is lower than the second steady state Serum Value of testosterone.

Following the first titration, about 400 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 600 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 400 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 200 mg TU daily to the subject to establish a third steady state Serum Value of testosterone that is lower than the second steady state Serum Value of testosterone.

Following the first titration, about 200 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 400 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 200 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 100 mg TU daily to the subject to establish a third steady state Serum Value of testosterone that is lower than the second steady state Serum Value of testosterone.

In some embodiments, following the second titration: the dosage may be increased to about 800 mg TU and the first dose includes about 400 mg TU, and the second dose includes about 400 mg TU. In some embodiments, the dosage may be decreased to about 100 mg TU and the subject receives a single dose of about 100 mg TU. The single dose of about 100 mg TU may be administered in the morning.

The first Serum Value of testosterone may be measured once steady state has been achieved. For example, the first Serum Value of testosterone may be measured prior to day 21, e.g., on from about day 1 to about day 21 (e.g., day 1, 2, 3, 4, 5, 6, 7, 8, 9, 10, 11, 12, 13, 14, 15, 16, 17, 18, 19, 20, or 21, e.g., 14) of a treatment regimen. The first Serum Value of testosterone may be measured on from about day 30 to about day 60 (e.g., day 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) of a treatment regimen.

The first titration may be performed any time after the first Serum Value of testosterone is measured, e.g., on from about day 1 to about day 35, e.g., on from about day 7 to about day 35, e.g., from about day 21 to about day 35 (e.g., day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, e.g., 28) of the treatment regimen. The first titration may be performed on from about day 30 to about day 60 (e.g., day 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) of a treatment regimen.

For example, the first Serum Value of testosterone may be measured on about day 14 of the treatment regimen and/or the first titration may be performed on about day 28 of the treatment regimen. A second Serum Value of testosterone may be measured. For example, the second Serum Value of testosterone may be measure on from about day 35 to about day 49 (e.g., day 35, 36, 37, 38, 39, 40, 41, 42, 43, 44, 45, 46, 47, 48, or 49, e.g., 42) of the treatment regimen.

A second titration may be performed, e.g., following the second Serum Value of testosterone measurement. The second titration may be performed on from about day 49 to about day 63 (e.g., day 49, 50, 51, 52, 53, 54, 55, 56, 57, 58, 59, 60, 61, 62, or 63, e.g., 56) of the treatment regimen. For example, the second Serum Value of testosterone may be measured on about day 42, and the second titration may be formed on about day 56.

In some embodiments, the first titration may be performed on about day 28 of the treatment regimen, and/or the second titration may be performed on about day 56 of the treatment regimen.

In some embodiments, the first titration may be performed, e.g., on from about day 21 to about day 35 (e.g., day 21, 22, 23, 24, 25, 26, 27, 28, 29, 30, 31, 32, 33, 34, or 35, e.g., 28) of the treatment regimen. Following the first titration, the second steady state Serum Value of testosterone may be established. Then, a second Serum Value of testosterone may be measured. A second titration may then be performed.

The subject has not previously been administered TU or other testosterone replacement therapies (e.g., a prodrug of TU) for a period of at least seven days (e.g., 2 weeks, 3 weeks, 4 weeks, 2 months, 3 months, 4 months, 5 months, 6 months, 1 year, or more). For example, the period may be sufficient to wash out all exogenous testosterone from the body.

In some embodiments, the method is performed on a population of human subjects. The population of subjects may include, e.g., at least 10 subjects, at least 50 subjects, at least 100 subjects, at least 200 subjects, at least 500 subjects, or more.

In some embodiments, the method achieves a Cavg in the serum normal range of about 300 ng/dL to about 1000 ng/dL in at least 75% of the population; achieves a Cmax of less than about 1500 ng/dL in at least 85% of the population; achieves a Cmax of from about 1800 ng/dL to about 2500 ng/dL in no more than 5% of the population; and/or achieves a Cmax of greater than about 2500 ng/dL in no more than 0% of the population.

In some embodiments, the method reduces an average number of incorrect titrations or the risk of incorrect titrations per subject in the population in order to achieve a steady state testosterone Serum Value of from about 300 ng/dL to about 1000 ng/dL relative to a population receiving a treatment regimen in which an initial dosage is not about 400 mg TU and/or the Serum Value is not measured from about 3 hours to about 6 hours after administration.

In some embodiments, the method achieves a Cavg in the serum normal range of about 300 ng/dL to about 1000 ng/dL in a greater number of subjects in the population as compared to a treatment regimen in which an initial dosage is not about 400 mg TU and/or the Serum Value is not measured from about 3 hours to about 6 hours after administration; achieves a Cmax of less than about 1500 ng/dL in a greater number of subjects in the population as compared to the treatment regimen in which the initial dosage is not about 400 mg TU and/or the Serum Value is not measured from about 3 hours to about 6 hours after administration; achieves a Cmax of from about 1800 ng/dL to about 2500 ng/dL in a fewer number of subjects in the population as compared to the treatment regimen in which the initial dosage is not about 400 mg TU and/or the Serum Value is not measured from about 3 hours to about 6 hours after administration; and/or achieves a Cmax of greater than about 2500 ng/dL in a fewer number of subjects in the population as compared to the treatment regimen in which the initial dosage is not about 400 mg TU and/or the Serum Value is not measured from about 3 hours to about 6 hours after administration.

In some embodiments, the method decreases the risk of elevated blood pressure, e.g., in the population of human subjects. For example, in some embodiments, daytime systolic blood pressure, night time systolic blood pressure, and/or 24-hour average systolic blood pressure does not increase by more than about 5 mmHg (e.g., no more than about 4, 3, or 2 mmHg) relative to baseline. In some embodiments, daytime systolic blood pressure, night time systolic blood pressure, and/or 24-hour average systolic blood pressure does not increase by more than about 3 mmHg relative to baseline. In some embodiments, daytime systolic blood pressure, night time systolic blood pressure, and/or 24-hour average systolic blood pressure does not increase by more than about 2 mmHg relative to baseline when measured by ambulatory blood pressure monitoring (ABPM).

The pharmaceutical composition may include from about 5% to about 40% (e.g., about 5%, 10%, 15%, 20%, 25%, 30%, 35%, 40%, e.g., about 18.2%) by weight TU. The pharmaceutical composition may include about from about 2% to about 45% (e.g., about 2%, 5%, 10%, 15%, 20%, 25%, 30%, 35%, 40%, or 45%, e.g., about 25%) by weight of a phytosterol or phytosterol ester. The phytosterol may include phytosterols, phytosterol esters, or combinations thereof. The pharmaceutical composition may include phytosterol esters. The formulation may include from about 10% to about 90% (e.g., about 10%, 15%, 20%, 25%, 30%, 35%, 40%, 45%, 50%, 55%, 60%, 65%, 70%, 75%, 80%, 85%, or 90%) by weight of a non-sterol solubilizing agent. The non-sterol solubilizing agent may be selected from lipids, surfactants (e.g., hydrophobic and/or hydrophilic surfactants), and mixtures thereof. The pharmaceutical composition may be self-emulsifying or self-microemulsifying.

In some embodiments, the non-sterol solubilizing agent includes propylene glycol monolaurate.

In some embodiments, the non-sterol solubilizing agent includes polyoxyl 40 hydrogenated castor oil.

In some embodiments, the pharmaceutical composition includes from about 10% to about 25% (e.g., about 15%, 20%, or 25%, e.g., about 18.2%) by weight of solubilized testosterone undecanoate; from about 5% to about 40% (e.g., about 10%, 15%, 20%, 25%, 30%, 35%, or 40%, e.g., about 15%) by weight of a hydrophilic surfactant; from about 15% to about 65% (e.g., about 20%, 25%, 30%, 35%, 40%, 45%, 50%, 55%, 60%, or 65%, e.g., about 39.9%) by weight of a hydrophobic surfactant; from about 2% to about 45% (e.g., about 2%, 5%, 10%, 15%, 20%, 25%, 30%, 35%, 40%, or 45%, e.g., about 25%) by weight of phytosterol esters; and from about 0 to about 15% (e.g., about 1%, 2%, 3%, 4%, 5%, 10%, or 15%, e.g., about 2%) by weight of a solubilizer.

In some embodiments, oral formulation includes from about 10% to about 40% (e.g., from about 10% to about 30%, e.g., about 25%) by weight of one or more phytosterol esters.

In some embodiments, the solubilizer includes dl-alpha-tocopherol and/or an ester or acetate thereof.

In some embodiments, the pharmaceutical composition includes: about 18.2% by weight of solubilized testosterone undecanoate; about 15.0% by weight of polyoxyl 40 hydrogenated castor oil; about 39.9% by weight of propylene glycol monolaurate; about 25.0% by weight of one or more phytosterol esters; and about 2.0% by weight of dl-alpha-tocopherol and/or an ester or acetate thereof.

In some embodiments of any of the above aspects, the first Serum Value and/or the second Serum Value is measured by measuring testosterone concentration of serum clotted at room temperature for about 30 minutes prior to centrifugation in a tube, measuring testosterone concentration of plasma in a tube supplemented with EDTA and NaF and multiplying the testosterone concentration by the inverse of a predetermined factor F (1/F), or a comparable method thereof. The predetermined factor may be, for example from about 0.70 to about 1.10, e.g., about 0.81 to about 0.94 (e.g., 0.81, 0.82, 0.83, 0.84, 0.85, 0.86, 0.87, 0.88, 0.89, 0.90, 0.91, 0.92, 0.93, or 0.94). For example, the predetermined factor may be 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10.

In one embodiment, the predetermined factor is 0.82. In one embodiment, the predetermined factor is 0.83. In one embodiment, the predetermined factor is 0.88. In one embodiment, the predetermined factor is 0.89. In another embodiment, the predetermined factor is 0.92.

Definitions

As used herein, the term "about" refers to a value that is +/−10% of a recited value. For example, a dose of about 400 mg TU refers to a dose that contains from 360 mg to 440 mg of TU. When referring to days, the term about refers to a value of +/−3 days. For example, an event (e.g., a serum T measurement or a dose titration) that occurs on about day 14 may occur from day 11 to day 17.

As used herein, the term "phytosterol" refers to a class of plant sterol molecules, which are naturally occurring compounds found in plant cell membranes. Phytosterols include both plant sterols and stanols. Phytosterols may be derived from any common plant source, such as soy, wood, tall oil, vegetable oil, and the like. Phytosterols include, for example, β-sitosterol, campesterol, stigmasterol, stigmastanol, campestanol, brassicasterol, ergosterol, lupeol, cycloartenol, and the like. Phytosterols also encompasses esterified derivatives thereof, sometimes referred to as phytosterol esters or phytostanol esters. Phytosterol esters are phytosterols esterified with a fatty acid, such as a long chain (e.g., $C_6$-$C_{24}$, e.g., $C_{10}$-$C_{24}$, e.g., $C_{14}$-$C_{24}$) fatty acid, such as octanoic acid, decanoic acid, undecanoic acid, lauric acid, myristic acid, palmitic acid, stearic acid, oleic acid, linoleic acid, and linolenic acid. Phytosterols and their esters may be fully saturated (e.g., hydrogenated). Commercially available phytosterols and phytosterol esters often comprise a mixture of different compounds. For example, CardioAid™ XF phytosterols, sold by ADM, include at least about 95% total plant sterols, about 40-58% β-sitosterol, about 20-30% campesterol, about 14-22% stigmasterol, about 0-6% brassicasterol, and about 0-5% sitostanol. COROWISE® plant sterols, sold by Cargill, include at least about 94% total plant sterols, about 40-58% β-sitosterol, about 20-28% campesterol, and about 16-23% stigmasterol. Tall oil derived phytosterols may include about 36-79% sitosterol, about 6-34% sitostanol, about 4-25% campesterol, and about 0-14% campestanol. Wood derived phytosterols may include about 72% sitosterol, about 8.2% campesterol, about 0.3% stigmasterol, about 0% brassicasterol, about 15.3% sitostanol, and about 1.6% campestanol. Vegetable oil derived phytosterols may include about 45% sitosterol, about 26.8% campesterol, about 19.3% stigmasterol, about 1.6% brassicasterol, about 2.1% sitostanol, and about 0.8% campestanol. Pharmaceutical compositions containing phytosterols or their esters may include one or more of the foregoing components or a mixture thereof. As used herein, the term "phytosterol" or "phytosterols" encompasses both phytosterols and phytosterol esters.

As used herein, "titration" refers to an increase or decrease of the total daily dosage of testosterone undecanoate administered to a subject, typically based on the response of the subject to the exogenous administered testosterone undecanoate. The dosage can be increased or decreased based on the measurement of serum testosterone concentration after a steady state has been achieved.

As used herein, "steady state" refers to the achievement of a stable response in serum total testosterone levels to exogenously administered testosterone undecanoate, typically achieved after at least 7 (e.g., 8, 9, 10, 11, 12, 13, 14, 15, 16, 17, 18, 19, 20, 21, or 28) days following the start of a dosing regimen.

In some embodiments, the titration can also include the adjustment of the way the total dosage is administered such as whether it is administered as two or three doses within a 24-hour period, whether it is administered with a meal, with a meal with a particular fat content, or at a particular hour of the day.

The terms "plasma testosterone concentration" and "serum testosterone concentration" refer to the "total" testosterone concentration which is the sum of the bioavailable testosterone including free and protein-bound testosterone concentrations, in plasma and serum, respectively. As with any bio-analytical measure, for increased consistency the method employed to measure initial serum testosterone levels should be consistent with the method used to monitor and re-measure serum testosterone levels during clinical testing and testosterone therapy for a subject.

As used herein, of the average plasma or serum testosterone concentration can be determined using methods and practices known in the art. For example, the average baseline plasma or serum testosterone concentration of a human male is the arithmetic mean of the total plasma or serum testosterone concentrations, respectively, determined on at least two consecutive time points that are reasonably spaced from each other, for example from about 1 hour to about 168 hours apart. In one example, the serum or plasma testosterone concentration can be determined on at least two consecutive times that are about 12 hours to about 48 hours apart. In another example, the plasma or serum testosterone concentration of the human male can be determined at a time between about 5 o'clock and about 11 o'clock in the morning. Further, the plasma or serum testosterone concentration can be the determined by standard analytical procedures and methods available in the art, such as for example, automated or manual immunoassay methods, liquid chromatography or liquid chromatography-tandem mass spectrometry (LC-MS/MS) and the like.

As used herein, the term "Serum Value" refers to a specified Cavg serum concentration testosterone and a corresponding plasma testosterone concentration. The serum concentration is multiplied by a predetermined factor (F) to convert the serum concentration into the corresponding plasma concentration such that:

F*(serum concentration)=plasma concentration; and

Serum Value=serum concentration=(1/F)*(plasma concentration).

As serum and plasma measurements of testosterone yield different values depending on the assay used for measurement, a predetermined factor F is needed to correlate measurements using different assays. The predetermined factor is calculated empirically and may be from, e.g., from about 0.70 to about 1.10, e.g., from about 0.81 to about 0.94 (e.g., 0.81, 0.82, 0.83, 0.84, 0.85, 0.86, 0.87, 0.88, 0.89, 0.90, 0.91, 0.92, 0.93, or 0.94). The predetermined factor may be 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, or 1.10. In one particular embodiment, the predetermined factor is about 0.89 when the plasma measurement is conducted using plasma sample tubes containing NaF/EDTA. In this embodiment, a Serum Value of about 300 ng/dL refers to a serum concentration of testosterone of about 300 ng/dL and a NaF/EDTA plasma concentration of testosterone of about 267 ng/dL (300 multiplied by 0.89 ng/dL). A Serum Value of about 1000 ng/dL refers to a serum concentration of testosterone of about 1000 ng/dL and a NaF/EDTA plasma concentration of testosterone of about 1000 multiplied by 0.89 ng/dL, which is about 890 ng/dL. The NaF/EDTA plasma concentrations of testosterone used as cutoffs for titration decisions of 400 ng/dL and 900 ng/dL may refer to Serum Values of (400/0.89)=449 ng/dL and (900/0.89)=1011 ng/dL, respectively. One of skill in the art would appreciate that due to the error associated with an empirically derived factor, these values can fluctuate within a reasonable error of, e.g., about +/-0 10%. A Serum Value may be obtained by measuring testosterone concentration of serum clotted at room temperature for about 30 minutes prior to centrifugation in a tube, measuring testosterone concentration of plasma in a tube supplemented with EDTA and NaF and multiplying the testosterone concentration by a predetermined factor F, or a comparable method thereof. Exemplary methods are described, e.g., in Lachance et al. *Future Sci OA*, FSO55, 2015, hereby incorporated by reference in its entirety.

In another embodiment, a linear regression is used to derive an equation that may be used to relate serum and plasma concentrations such that:

$$F^*(\text{serum concentration}-b) = \text{plasma concentration; and}$$

$$\text{Serum Value} = \text{serum concentration} = (1/F)^*(\text{plasma concentration}) + b;$$

where b is the y-intercept in the linear regression and 1/F is the slope.

As serum and plasma measurements of testosterone yield different values depending on the assay used for measurement, a predetermined linear equation is needed to correlate measurements using different assays. For example, the slope 1/F may be 1.023 and the intercept 50.45 ng/dL. In one particular embodiment, the predetermined slope is about 1.023 and the intercept is 50.45 ng/dL when the plasma measurement is conducted using plasma sample tubes containing NaF/EDTA. In this embodiment, a Serum Value of about 300 ng/dL refers to a serum concentration of testosterone of about 300 ng/dL and a NaF/EDTA plasma concentration of testosterone of about 244 ng/dL (300, minus the intercept 50.45, and the resultant divided by 1.023). A Serum Value of about 1000 ng/dL refers to a serum concentration of testosterone of about 1000 ng/dL and a NaF/EDTA plasma concentration of testosterone of about 928 ng/dL (1000, minus the intercept 50.45, and the resultant divided by 1.023). The NaF/EDTA plasma concentrations of testosterone used as cutoffs for titration decisions of 400 ng/dL and 900 ng/dL may refer to Serum Values of (400*1.023)+50.45=460 ng/dL and (900*1.023)+50.45=971 ng/dL, respectively (see, e.g., FIG. 8). One of skill in the art would appreciate that due to the error associated with an empirically derived factor, these values can fluctuate within a reasonable error of, e.g., about +/-10%. A Serum Value may be obtained by measuring testosterone concentration of serum clotted at room temperature for about 30 minutes prior to centrifugation in a tube, measuring testosterone concentration of plasma in a tube supplemented with EDTA and NaF and using the linear equation to convert to a serum value, or a comparable method thereof.

One of skill in the art would also appreciate that the parameters of the linear equation used may be dependent on the analytical methodology of the assay for testosterone. For example, immunoassay may have different selectivity and parameters suitable for relating serum and plasma concentrations may be similarly obtained.

Additionally, one of skill in the art would also appreciate that more refined equations relating the serum and plasma concentrations may be applied to the empirical relationship. For example, a non-linear equation could be used to describe the relationship of serum and plasma concentrations.

As used herein, the term $AUC_{0-t}$ is the area under the curve of a plasma-versus-time graph determined for the analyte from the time 0 to time "t".

As used herein, the terms "Cavg" or "$C_{avg-t}$" is determined as the $AUC_{0-t}$ divided by a predetermined period of time (t). For example, $C_{avg-8h}$ is the average plasma concentration over a period of 8 hours post-dosing determined by dividing the $AUC_{0-8}$ value by 8. Similarly, $C_{avg-12h}$ is the average plasma concentration over a period of 12 hours post-dosing determined by dividing the $AUC_{0-12}$ value by 12; $C_{avg-24h}$ is the average plasma concentration over a period of 24 hours post-dosing determined by dividing the $AUC_{0-24h}$ value by 24, and so on. Unless otherwise stated, all $C_{avg}$ values are considered to be $C_{avg-24h}$.

As used herein, "$C_t$" refers to the serum concentration of testosterone at time "t" prior to or after administration of the dosage of the current invention. The time "t" is generally in hours, unless otherwise specified. For example, a $C_t$ of "$C_{(-2\ to\ 0)}$" refers to serum testosterone concentration measured in sample collected between the time of about 2 hours before and just immediately prior to dosage administration to the subject tested. Similarly, $C_t$ of "$C_{(2\ to\ 4)}$" refers to serum testosterone concentration measured in sample collected between the time of about 2 hours and 4 hours after administration of a dosage to the subject tested.

As used herein, a PK parameter (e.g., Cavg or Cmax), may be a parameter that is measured in a population of subjects, e.g., who are treated with a TU formulation, e.g., as part of a clinical trial.

As used herein, a "population of subjects" refers to a group of at least 10 (e.g., at least 15, 20, 25, 30, 35, 40, 45, 50, 60, 70, 80, 90, 100, 150, 200, 250, 300, 350, 400, 450, 500, or more) subjects.

As used herein, a "subject" refers to an animal, such as a human subject. The subject may be a male. The subject may be a hypogonadal male.

DETAILED DESCRIPTION

Figure 1:
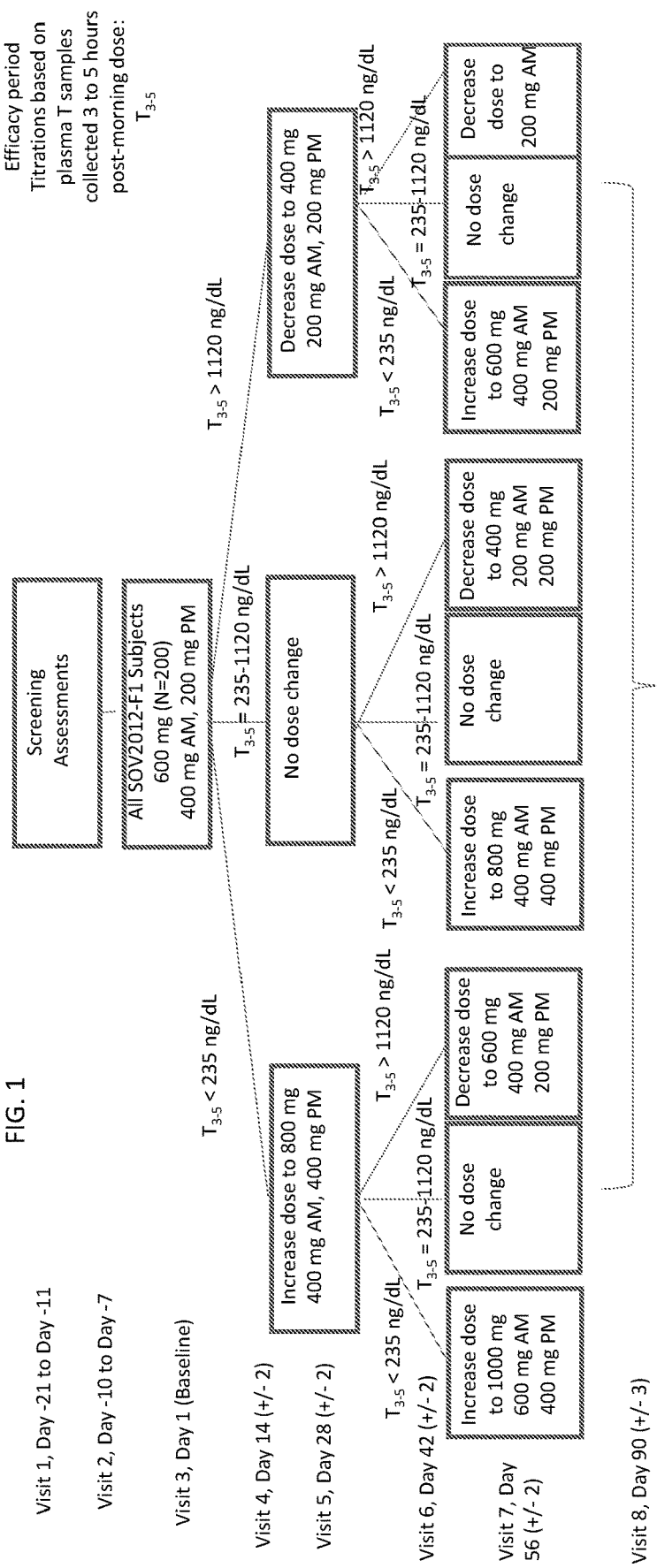
FIG. 1 is a graphic representation of Study 1 SOV2012-F1 dose titration in the study. Abbreviations: a.m.=morning; N=number of subjects; p.m.=evening; T3-5=plasma testosterone concentration measured between 3 and 5 hours (+10 min) post-morning dose. [a]The investigator and the sponsor will review the data for each individual, and the reason for not responding to treatment will be investigated. Assuming correct compliance with study drug, SOV2012-F1 may be increased to 600 mg a.m., 400 mg p.m. at the investigator's discretion, taking safety into consideration, or subjects may be discontinued from the study as non-responders. Data will be reported in the clinical study report.

The present invention features new methods for treating testosterone deficiency. In particular, the invention features testosterone undecanoate (TU) dosing regimens that include administration of TU, performing a plasma or serum measurement of testosterone (T), and titrating the dosage (e.g., increasing or decreasing the dosage) if necessary, in order to achieve favorable pharmacokinetic (PK) parameters. Favorable PK parameters may also be obtained without titrating the dosage. Obtaining favorable PK parameters is necessary to achieve FDA approval for testosterone replacement therapy. Currently, the FDA guidelines for testosterone replacement therapy require testosterone blood serum concentrations (Cavg) in the normal range of 300 to 1000 ng/dL in 75% of subjects, maximum T blood serum concentrations (Cmax) less than 1500 ng/dL in 85% of subjects, not more than 5% between 1800 and 2500 ng/dL, and none above 2500 ng/dL. It should be noted that the FDA guidelines are in fact a guideline, and one of skill in the art would appreciate that they could change or become less rigid. For example, another commonly accepted definition of a normal range is from about 264 ng/dL to about 917 ng/dL. Furthermore, it may be that some subjects do, in fact, exhibit a serum Cmax above 2500 ng/dL. However, the goal is to produce as few subjects as possible above this threshold.

In general, the goal is to design a dosing strategy that reduces the number of titrations and serum T measurements in order to simplify the administration, increase patient compliance, and obtain a serum T concentration in a range consistent with normal subjects (e.g., non-hypogonadal males) and reflective of the FDA guidelines, while providing a safe and efficacious therapy. Furthermore, when a titration is performed, it is also desirable to make a correct titration decision such that the you do not have to adjust the dosage one or more times. For example, if one were administered a dosage of TU and a serum T concentration was measured that is below the normal range, then it may be desirable to increase the dosage. However, if the dosage were increased too high and the next serum T concentration measurement is above the normal range, then one may need to decrease the dosage. An additional goal is to reduce unwanted side effects associated with testosterone replacement therapy, such as elevated blood pressure. The methods described herein have been shown to satisfy the foregoing goals by minimizing blood pressure increases that may occur with testosterone replacement therapy and reducing incorrect titration decisions.

Surprisingly, we discovered that using the starting dosages of TU described herein, measuring the serum or plasma concentration of T from about 3 hours to about 5 hours after a dosing event, and titrating the dosage of TU within a predetermined range following the plasma or serum measurement led to improved PK performance in treated subjects, a higher number of correct titration decisions, a lower number of incorrect titration decisions, and a lower risk of increased blood pressure and/or heart rate. Furthermore, using a NaF/EDTA plasma Cavg concentration range of about 400 ng/dL to about 900 mg/dL (e.g., a serum Cavg concentration range of about 449 ng/dL to about 1011 ng/dL if F is 0.89 or from about 460 ng/dL to about 971 ng/dL if the slope 1/F is 1.023 and b is 50.45) to trigger titration decisions may provide a more favorable outcome as compared to a Cavg concentration range of about 300 ng/dL to about 1000 ng/dL. The preferred starting dosages of TU and particular days on which to perform a serum or plasma measurement and implement a dosage titration are described in more detail below. Also surprisingly, we discovered that the present treatment regimen provides lower risk of increased blood pressure and heart rate. This may negate the need for subsequent blood pressure or heart rate medications required by a subject undergoing testosterone replacement therapy.

Even further, we also discovered that testosterone values are reliably measured in a window from about 3 hours to about 6 hours (e.g., about 3 hours to about 5 hours) following administration of the TU formulation (e.g., following the morning dose). This window provides a robust measurement window for single measurement evaluation. This feature may be due to the phytosterol esters within the formulation, e.g., due to presence of flat PK curve post dosing, e.g., due to modified release, that permits reliable assessment of subject in the sample window (see FIG. 7). By providing a reliable window in this range, this in turn imparts reliable titration decisions and results, with potential to yield more accurate titration decisions, and reduce unwanted side-effects, such as blood pressure elevation and increased heart rate.

Dosage and Administration

Described herein are formulations and methods for oral administration of testosterone undecanoate. The oral dosage formulations (e.g., capsule, softgel, tablet, lozenge, syrup, or the like) can be used to treat a subject (e.g., a human, e.g., male human subject). The subject may suffer from testosterone deficiency, such as hypogonadism. Accordingly, the methods described herein provide a serum concentration of testosterone within a target serum testosterone concentration $C_{ave}$ range for a subject (e.g., a male subject) or a population of subjects. The method includes the step of orally administering to the subject a dosage of a pharmaceutical composition containing TU.

The formulation may include TU at about 5% to about 40% (e.g., about 5% to about 35%, about 5% to about 25%, about 5% to about 20%, about 10% to about 35%, about 10% to about 25%, about 10% to about 20%, about 10% to about 15%, about 15% to about 35%, about 15% to about 30%, about 15% to about 25%, about 15% to about 20%) by weight (wt %) of the formulation. For example, the formulation may contain about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 29%, or 40% by weight of the formulation. The pharmaceutical composition may provide a dosage of about 25 mg to about 1000 mg (e.g., about 50 mg to about 600 mg, about 100 mg to about 600 mg, about 200 mg to about 600 mg, about 200 mg to about 400 mg, about 100 mg to about 200 mg) TU per day. For example, the formulation may provide about 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg TU per day.

A pharmaceutical composition may be administered in multiple doses. For example, it is understood that all dosages may be continuously given or divided into multiple doses given per a given time frame. For example, a daily dosage of about 400 mg may be administered in two doses, (e.g., a first dose of about 200 mg and a second dose of about 200 mg, or a first dose of about 100 mg and a second dose of about 300 mg).

The pharmaceutical compositions described herein may be administered one or more times per day. For example, a dose may be administered once per day, twice per day, three times per day, four times per day, five times per day, six times per day, or more. The formulation may be administered with a meal.

Formulations and Excipients

The formulations used in the methods described herein are provided in a self-emulsifying drug delivery system (SEDDS), self-microemulsifying drug delivery system (SMEDDS), or self-nanoemulsifying drug delivery system (SNEDDS) delivery system, which are known in the art as useful mechanisms for delivery of hydrophobic drugs, such as TU. Hydrophobic drugs are associated with poor water solubility and low oral bioavailability. SEDDS/SMEDDS/SNEDDS formulations are isotropic mixtures of an oil, a surfactant, a cosurfactant (or solubilizer), and a drug. The basic principle of this system is its ability to form fine oil in-water (o/w) microemulsions under gentle agitation following dilution by aqueous phases (e.g., the digestive motility of the stomach and intestine provide the agitation required for self-emulsification in vivo in the lumen of the gut). This spontaneous formation of an emulsion in a fluid environment, such as the gastrointestinal tract presents the drug in a solubilized form, and the small size of the formed droplet provides a large interfacial surface area for drug absorption. Apart from solubilization, the presence of lipid in the formulation further helps improve bioavailability by affecting the drug absorption. Selection of a suitable self-emulsifying formulation depends upon the assessment of the solubility of the drug in various components, the area of the self-emulsifying region as obtained in the phase diagram, the droplet size distribution of the resultant emulsion following self-emulsification, and the release rate of the drug after dispersion in intestinal fluids.

The formulations described herein include TU. TU may be formulated with a non-sterol solubilizing agent, and one or more phytosterols or phytosterol esters. The non-sterol solubilizing agent may include one or more hydrophobic surfactants, one or more hydrophilic surfactants, and/or mixtures thereof.

A lipophilic or hydrophobic surfactant as defined herein is poorly water soluble or water insoluble and has a hydrophilic-lipophilic balance (HLB) value of less than 10, preferably less than 5 and more preferably a HLB of 1 to 3. HLB is an empirical expression for the relationship of the hydrophilic and hydrophobic groups of a surface-active amphiphilic molecule, such as a surfactant. It is used to index surfactants and its value varies from about 1 to about 45 and includes both non-ionic and ionic surfactants. It is well known that the higher the HLB, the more water soluble/dispersible the surfactant.

Exemplary lipophlic surfactants include, but are not limited to, Maisine 35-1, Imwitor 742, Capmul MCM, Capmul PG 12, Lauroglycol 90, Lauroglycol FCC, Caproyl 90, Captex 250, a fatty acid selected from the group consisting of octanoic acid, decanoic acid, undecanoic acid, lauric acid, myristic acid, palmitic acid, stearic acid, oleic acid, linoleic acid, and linolenic acid. Fatty acids may include both a lipophilic and hydrophilic component, and therefore, may be characterized as either a lipophilic or hydrophilic surfactant. As used herein, a lipophilic surfactant may also be referred to as a poorly water-soluble surfactant or a hydrophobic surfactant.

Lipophilic surfactants suitable for use in the formulations described herein include, for example, fatty acids ($C_6$-$C_{24}$, e.g., $C_{10}$-$C_{24}$, e.g., $C_{14}$-$C_{24}$), for example, octanoic acid, decanoic acid, undecanoic acid, lauric acid, myristic acid, palmitic acid, stearic acid, oleic acid, linoleic acid, and linolenic acid.

Lipophilic surfactants suitable for use in the formulations described herein include, for example, mono- and/or di-glycerides of fatty acids, such as Imwitor 988 (glyceryl mono-/di-caprylate), Imwitor 742 (glyceryl mono-/di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl mono-/di-caprylate/caprate), Capmul MCM(L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soybean oil), Precirol ATO 5 (glyceryl palmitostearate) and Gelucire 39/01 (semi-synthetic glycerides, e.g., $C_{12\text{-}18}$ mono-, di- and tri-glycerides).

Lipophilic surfactants suitable for use in the formulations described herein include, for example, acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides).

Lipophilic surfactants suitable for use in the formulations described herein include, for example, propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate).

Lipophilic surfactants suitable for use in the formulations described herein include, for example, polyglycerol esters of fatty acids such as Plurol oleique (polyglyceryl oleate), Caprol ET (polyglyceryl mixed fatty acids) and Drewpol 10.10.10 (polyglyceryl oleate).

Lipophilic surfactants suitable for use in the formulations described herein include, for example, castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil).

Lipophilic surfactants suitable for use in the formulations described herein include, for example, acid and ester ethoxylates formed by reacting ethylene oxide with fatty acids or glycerol esters of fatty acids (HLB<10) such as Crodet 04 (polyoxyethylene (4) lauric acid), Cithrol 2MS (polyoxyethylene (2) stearic acid), Marlosol 183 (polyoxyethylene (3) stearic acid) and Marlowet G12DO (glyceryl 12 EO dioleate).

Lipophilic surfactants suitable for use in the formulations described herein include, for example, sorbitan esters of fatty acids, for example, Span 20 (sorbitan monolaurate), Crill 1 (sorbitan monolaurate) and Crill 4 (sorbitan monooleate).

Lipophilic surfactants suitable for use in the formulations described herein include, for example, transesterification products of natural or hydrogenated vegetable oil triglyceride and a polyalkylene polyol (HLB<10), e.g., Labrafil M1944CS (polyoxyethylated apricot kernel oil), Labrafil M2125CS (polyoxyethylated corn oil), and Gelucire 37/06 (polyoxyethylated hydrogenated coconut).

Lipophilic surfactants suitable for use in the formulations described herein include, for example, alcohol ethyoxylates (HLB<10), e.g., Volpo N3 (polyoxyethylated (3) oleyl ether), Brij 93 (polyoxyethylated (2) oleyl ether), and Marlowet LA4 (polyoxyethylated (4) lauryl ether).

Lipophilic surfactants suitable for use in the formulations described herein include, for example, pluronics, for example, Polyoxyethylene-polyoxypropylene co-polymers and block co-polymers (HLB<10) e.g., Synperonic PE L42 (HLB=8) and Synperonic PE L61 (HLB=3).

In some embodiments, a mixture of lipophilic surfactants, e.g., as described above, may be used in the formulations described herein.

The formulations suitable for use in the methods described herein include any pharmaceutically acceptable hydrophilic surfactant (e.g., having an HLB value greater than 10). Some non-limiting examples include, castor oil or hydrogenated castor oil ethoxylates (HLB>10), e.g., Cremophor EL (polyoxyethylene (35) castor oil), Cremophor RH40 (polyoxyethylene (40) hydrogenated castor oil), Etocas 40 (polyoxyethylene (40) castor oil), Nikkol HCO-60 (polyoxyethylene (60) hydrogenated castor oil), Solutol HS-15 (polyethylene glycol 660 hydroxystearate), Labrasol (caprylocaproyl macrogol-8 glycerides), α-tocopherol-polyethylene glycol-1000-succinate (TPGS) and ascorbyl-6 palmitate.

Hydrophilic surfactants suitable for use in the formulations described herein include, for example, polyoxyethylene sorbitan fatty acid derivates, e.g., Tween 20 (polyoxyethylene (20) monolaureate), Tween 80 (polyoxyethylene (20) monooleate), Crillet 4 (polyoxyethylene (20) monooleate) and Montanox 40 (polyoxyethylene (20) monopalmitate).

Hydrophilic surfactants suitable for use in the formulations described herein include, for example, gelucires, preferably Gelucire 50/13 (PEG mono- and diesters of palmitic and stearic acids. (In reference to Gelucires, the first number (e.g., 50) corresponds to the melting point of the material and the second (e.g., 13) to the HLB number.)

Hydrophilic surfactants suitable for use in the formulations described herein include, for example, fatty acid ethoxylates (HLB>10), e.g., Myrj 45 (polyoxyethylene (8) stearate), Tagat L (polyoxyethylene (30) monolaurate), Marlosol 1820 (polyoxyethylene (20) stearate) and Marlosol OL15 (polyoxyethylene (15) oleate). Myrj 45 is preferred.

Hydrophilic surfactants suitable for use in the formulations described herein include, for example, alcohol ethoxylates (HLB>10), e.g., Brij 96 (polyoxyethylene (10) oleyl ether), Volpo 015 (polyoxyethylene (15) oleyl ether), Marlowet OA30 (polyoxyethylene (30) oleyl ether) and Marlowet LMA20 (polyoxyethylene (20) $C_{12}$-$C_{14}$ fatty ether).

Hydrophilic surfactants suitable for use in the formulations described herein include, for example, polyoxyethylene-polyoxypropylene co-polymers and block co-polymers (HLB>10), that are commercially available under the trade name Pluronics or Poloxamers, such as Poloxamers 188 and 407 also known as Syperonic PE L44 (HLB=16) and Syperonic F127 (HLB=22), respectively.

Hydrophilic surfactants suitable for use in the formulations described herein include, for example, anionic surfactants, e.g., sodium lauryl sulphate, sodium oleate, and sodium dioctylsulphosuccinate.

Hydrophilic surfactants suitable for use in the formulations described herein include, for example, alkylphenol surfactants (HLB>10), e.g., Triton N-101 (polyoxyethylene (9-10) nonylphenol) and Synperonic NP9 (polyoxyethylene (9) nonylphenol).

In some embodiments, a mixture of hydrophilic surfactants, e.g., as described above, may be used in the formulations described herein.

In some embodiments, a mixture of hydrophilic surfactants and lipophilic surfactants, e.g., as described above, may be used in the formulations described herein.

The formulations described herein may also include one or more additional cosolvents. Cosolvents suitable with the formulations described herein, include, for example, short chain mono-, di-, and polyhydric alcohols, such as ethanol, benzyl alcohol, glycerol, propylene glycol, propylene carbonate, polyethylene glycol with an average molecular weight of about 200 to about 10,000, diethylene glycol monoethyl ether (e.g., Transcutol HP), and combinations thereof. In some embodiments, the formulation further includes water.

The formulations described herein may include an additional oil. Additional oils that may be incorporated in embodiments of the present invention include complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of oils for use in this invention thus include: vegetable oils (e.g., soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (e.g., fish liver oil, shark oil, and mink oil).

In some preferred embodiments, the formulations suitable for use in the methods described herein include TU, a non-sterol solubilizing agent, and a phytosterol or phytosterol ester, or a mixture thereof. For example, the formulation may include about 5% to about 40% TU, about 10% to about 90% of a non-sterol solubilizing agent, and about 2% to about 45% by weight of a phytosterol or phytosterol ester. For example, the formulation may include about 5% to about 40% (e.g., about 5% to about 35%, about 5% to about 25%, about 5% to about 20%, about 10% to about 35%, about 10% to about 25%, about 10% to about 20%, about 10% to about 15%, about 15% to about 35%, about 15% to about 30%, about 15% to about 25%, about 15% to about 20%) TU by weight of the formulation. The formulation may include about 10% to about 90% (e.g., about 10% to about 80%, about 10% to about 70%, about 10% to about 60%, about 10% to about 50%, about 10% to about 40%, about 10% to about 30%, about 10% to about 20%, about 20% to about 90%, about 20% to about 80%, about 20% to about 70%, about 20% to about 60%, about 20% to about 50%, about 20% to about 40%, about 20% to about 30%, about 30% to about 90%, about 30% to about 80%, about 30% to about 70%, about 30% to about 60%, about 30% to about 50%, about 30% to about 40%, about 40% to about 90%, about 40% to about 80%, about 40% to about 70%, about 40% to about 60%, about 40% to about 50%, about 50% to about 90%, about 50% to about 80%, about 50% to about 70%, about 50% to about 60%, about 60% to about 90%, about 60% to about 80%, about 60% to about 70%, about 70% to about 90%, about 70% to about 80%, or about 80% to about 90%) by weight of a non-sterol solubilizing agent. In some embodiments, the formulation may include about 10%, about 15%, about 20%, about 25%, about 30%, about 35%, about 40%, about 45%, about 50%, about 55%, about 60%, about 65%, about 70%, about 75%, about 80%, about 85%, or about 90% by weight of a non-sterol solubilizing agent. The formulation may include about 2% to about 45% by weight of a phytosterol or phytosterol ester, or a mixture thereof. For example, the formulation may include about 5% to about 35%, about 5% to about 25%, about 5% to about 20%, about 10% to about 35%, about 10% to about 25%, about 10% to about 20%, about 10% to about 15%, about 15% to about 35%, about 15% to about 30%, about 15% to about 25%, about 15% to about 20% by weight of a phytosterol or phytosterol ester. In some embodiments, the formulation includes about 5%, about 10%, about 15%, about 20%, about 25%, about 30%, about 35%, about 40%, or about 45% by weight of a phytosterol or phytosterol ester or a mixture thereof. The phytosterol can be selected from β-sitosterol, campesterol, stigmasterol, stigmastanol, campestanol, brassicasterol, ergosterol, lupeol, and cycloartenol. Similarly, the phytosterol ester can be a fatty acid ester of a phytosterol selected from β-sitosterol, campesterol, stigmasterol, stigmastanol, campestanol, brassicasterol, ergosterol, lupeol, and cycloartenol.

In some embodiments, the formulation includes from about 10% to about 25% (e.g., about 15% to about 25%, e.g., about 18.2%) by weight of solubilized testosterone undecanoate; from about 5 to about 40% (e.g., about 5% to about 30%, about 10% to about 20%, e.g., about 15.0%) by weight of a hydrophilic surfactant; from about 15% to about 65% (e.g., about 20% to about 60%, about 30% to about 50%, e.g., about 39.9%) by weight of a hydrophobic surfactant; from about 2% to about 45% (e.g., about 5% to about 40%, about 10% to about 30%, e.g., about 25.0%) about by weight of phytosterol esters; and from about 0 to about 15% (e.g., about 0 to about 10%, e.g., about 0 to about 5%, e.g., about 2.0%) by weight of a solubilizer.

In some embodiments, the hydrophilic surfactant is polyoxyl 40 hydrogenated castor oil (e.g., Cremophor RH40). In some embodiments, the hydrophilic surfactant is propylene glycol monolaurate (e.g., Lauroglycol 90). In some embodiments, the solubilizer is dl-alpha tocopherol (e.g., vitamin E) and/or an ester or acetate thereof. In some embodiments, the formulation includes about 18.2% by weight of solubilized testosterone undecanoate; about 15.0% by weight of polyoxyl 40 hydrogenated castor oil; about 39.9% by weight of propylene glycol monolaurate; about 25.0% by weight of one or more phytosterol esters; and about 2.0% by weight of dl-alpha-tocopherol and/or an ester or acetate thereof.

Titration

The methods described herein include adjusting a dosage of TU in order to optimize one or more PK parameters. The methods include administering to the subject a pharmaceutical composition including testosterone undecanoate (TU), a non-sterol solubilizing agent effective for solubilization of the TU, and a phytosterol or phytosterol ester. The subject has not previously been administered TU or other testosterone replacement therapies (e.g., a prodrug of TU) for a period of at least seven days (e.g., 2 weeks, 3 weeks, 4 weeks, 2 months, 3 months, 4 months, 5 months, 6 months, 1 year, or more). For example, the period may be sufficient to wash out all exogenous testosterone from the body.

The initial dosage of TU may be from about 100 mg to about 1000 mg TU (e.g., about 200 mg, 300 mg, 400 mg, 500 mg, 600 mg, 700 mg, 800 mg, 900 mg, or 1000). In some embodiments, the initial dosage is about 400 mg. This may be administered daily until a first steady state serum concentration of testosterone is achieved. The method may include providing a first Serum Value of testosterone in the subject following administration of the TU. Additionally, the method may further include performing a first titration of the testosterone undecanoate, e.g., if necessary. If the first Serum Value of testosterone is less than about 400/F ng/dL or 400/F+b ng/dL (e.g., a serum concentration of less than about 449 ng/dL or less than about 460 ng/dL or a plasma concentration of about 400 ng/dL), then the dosage may be increased, e.g., by about 25%, 50%, 100%, 150%, 200%, or more. For example, if the initial dosage is about 400 mg, then the dosage may be increased, e.g., to about 600 mg TU. This may establish a second steady state Serum Value of testosterone that is higher than the first Serum Value of testosterone. If the first Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the dosage may be maintained, e.g., at about 400 mg. This may maintain the first steady state Serum Value of testosterone. If the first Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the dosage may be decreased, e.g., by about 25%, 50%, 100%, 150%, 200%, or more. For example, if the initial dosage is about 400 mg, then the dosage may be decreased, e.g., to about 200 mg TU. This may establish a second steady state Serum Value of testosterone that is lower than the first Serum Value of testosterone (see FIG. 6).

When a titration is performed, the dosage of TU may be increased, decreased, or maintained. The dosage may increase by about 50 mg, 100 mg, 150 mg, 200 mg, 250 mg, or 300 mg. The dosage may decrease by about 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

A serum or plasma concentration measurement may be performed any time following initiation of TU treatment. For example, a serum or plasma concentration may be measured 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, or more following initiation of TU administration during a treatment regimen.

A titration may be performed any time following an initial administration of TU during a treatment regimen. A titration may be in response to a serum or plasma concentration measurement that occurs following an initial administration of TU during a treatment regimen. For example, a titration may be performed 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, or more following a serum or plasma concentration measurement. In some embodiments, a titration may be performed 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, or more following an initial administration of TU during a treatment regimen.

The Serum Value of testosterone may be measured after administration of TU. For example, the plasma or serum T concentration may be measured from about 3 hours to about 5 hours (e.g., 3 hours, 4 hours, or 5 hours) after administration. The plasma or serum T concentration may be measured after the morning dose. In some embodiments, the plasma or serum T concentration may be measured from about 3 hours to about 6 hours after administration. The pharmaceutical composition may be administered with a meal. Alternatively, the pharmaceutical composition may be administered without a meal. The pharmaceutical composition may be administered in two or more (e.g., 2, 3, 4, 5, 6, 7, 8, 9, 10, or more) doses. The pharmaceutical composition may be administered in two doses per day (e.g., twice daily administration). A first dose may be administered in the morning, and a second dose may be administered in the evening. The doses may be equal. Alternatively, the doses may be different. For example, when administered a daily dosage of about 400 mg TU, the first dose may include about 200 mg TU, and the second dose may include about 200 mg TU.

In some embodiments, following the first titration: the dosage may be increased to about 600 mg TU, and the first dose includes about 300 mg TU, and the second dose includes about 300 mg TU; the dosage may be maintained at about 400 mg TU, and the first dose includes about 200 mg TU, and the second dose includes about 200 mg TU; or the dosage may be decreased to about 200 mg TU, and the first dose includes about 100 mg TU, and the second dose includes about 100 mg TU.

In some embodiments, the method further includes providing a second Serum Value of testosterone.

In some embodiments, the method further includes performing a second titration, e.g., following the second Serum Value of testosterone measurement.

Following the first titration, about 600 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 800 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 600 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 400 mg TU daily to the subject to establish a third steady state Serum Value of testosterone that is lower than the second steady state Serum Value of testosterone.

Following the first titration, about 400 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 600 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 400 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 200 mg TU daily to the subject to establish a third steady state Serum Value of testosterone that is lower than the second steady state Serum Value of testosterone.

Following the first titration, about 200 mg TU may be administered daily to the subject. If the second Serum Value of testosterone is less than about 400/F ng/dL or 400/F+b ng/dL (e.g., a serum concentration of less than about 449 ng/dL or less than about 460 ng/dL or a plasma concentration of less than about 400 ng/dL), then the method may include orally administering about 400 mg TU daily to the subject to establish a third steady state Serum Value of testosterone that is higher than the second steady state Serum Value of testosterone. If the second Serum Value of testosterone is from about 400/F ng/dL to about 900/F ng/dL or from about 400/F+b ng/dL to about 900/F+b ng/dL (e.g., a serum concentration of from about 449 ng/dL to about 1011 ng/dL or from about 460 ng/dL to about 971 ng/dL or a plasma concentration of from about 400 ng/dL to about 900 ng/dL), then the method may include continuing to orally administer about 200 mg TU daily to the subject to maintain the second steady state Serum Value of testosterone. If the second Serum Value of testosterone is greater than about 900/F ng/dL or 900/F+b ng/dL (e.g., a serum concentration of greater than about 1011 ng/dL or greater than about 971 ng/dL or a plasma concentration of greater than about 900 ng/dL), then the method may include orally administering about 100 mg TU daily to the subject to establish a third steady state Serum Value of testosterone that is lower than the second steady state Serum Value of testosterone.

In some embodiments, following the second titration: the dosage may be increased to about 800 mg TU and the first dose includes about 400 mg TU, and the second dose includes about 400 mg TU; or the dosage may be decreased to about 100 mg TU and the subject receives a single dose of about 100 mg TU. The single dose of about 100 mg TU may be administered in the morning or in the evening.

The first Serum Value of testosterone may be measured once steady stage has been achieved. For example. The first Serum Value of testosterone may be measured from day 1, e.g., on from about day 1 to about day 21, e.g., on from about day 7 to about day 21 (e.g., day 1, 2, 3, 4, 5, 6, 7, 8, 9, 10, 11, 12, 13, 14, 15, 16, 17, 18, 19, 20, or 21, e.g., 14) of a treatment regimen.

The first titration may be performed any time after the first Serum Value of testosterone is measured, e.g., on from about day 1 to about day 35, e.g., on from about day 7 to about day 35, e.g., on from about day 21 to about day 35 (e.g., day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, e.g., 28) of the treatment regimen. The first titration may be performed on from about day 30 to about day 60 (e.g., day 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) of a treatment regimen.

For example, the first Serum Value of testosterone may be measured on about day 14 of the treatment regimen and/or the first titration may be performed on about day 28 of the treatment regimen.

A second Serum Value of testosterone may be measured following the first titration, e.g., once a second steady state Serum Value has been achieved. For example, the second Serum Value of testosterone may be measure on from about day 35 to about day 49 (e.g., day 35, 36, 37, 38, 39, 40, 41, 42, 43, 44, 45, 46, 47, 48, or 49, e.g., 42) of the treatment regimen. A second titration may be performed, e.g., following the second Serum Value of testosterone measurement. The second titration may be performed on from about day 49 to about day 63 (e.g., day 49, 50, 51, 52, 53, 54, 55, 56, 57, 58, 59, 60, 61, 62, or 63, e.g., 56) of the treatment regimen. For example, the second Serum Value of testosterone may be measured on about day 42, and the second titration may be formed on about day 56.

In some embodiments, the first titration may be performed on about day 28 of the treatment regimen, and/or the second titration may be performed on about day 56 of the treatment regimen.

In some embodiments, the first titration may be performed, e.g., on from about day 21 to about day 35 (e.g., day 21, 22, 23, 24, 25, 26, 27, 28, 29, 30, 31, 32, 33, 34, or 35, e.g., 28) of the treatment regimen. Following the first titration, the second steady state Serum Value of testosterone may be established. Then, a second Serum Value of testosterone may be measured. A second titration may then be performed.

In some embodiments, the method decreases the risk of elevated blood pressure. For example, in some embodiments, daytime systolic blood pressure, night time systolic blood pressure, and/or 24-hour average systolic blood pressure does not increase by more than about 5 mmHg (e.g., no more than about 4, 3, or 2 mmHg) relative to baseline. In some embodiments, daytime systolic blood pressure, night time systolic blood pressure, and/or 24-hour average systolic blood pressure does not increase by more than about 3 mmHg relative to baseline. In some embodiments, daytime systolic blood pressure, night time systolic blood pressure, and/or 24-hour average systolic blood pressure does not increase by more than about 2 mmHg relative to baseline when measured by ambulatory blood pressure monitoring (ABPM). In some embodiments, the first Serum Value and/or the second Serum Value is measured by measuring testosterone concentration of serum clotted (e.g., at room temperature, e.g., for about 30 to about 50 minutes) prior to centrifugation in a tube, measuring testosterone concentration of plasma in a tube supplemented with EDTA and NaF and multiplying the testosterone concentration by the inverse of a predetermined factor F (1/F), or a comparable method thereof, such as an immunoassay. In some embodiments K2/EDTA tubes or other plasma tubes may be used.

The foregoing titration scheme may be advantageous over other titration schemes. For example, a starting dosage of about 400 mg TU may be advantageous over other starting dosages of TU, such as 800 mg, 700 mg, 600 mg, 500 mg, 300 mg, 200 mg, or 100 mg. A starting dosage of about 400 mg TU may be advantageous over a starting dosage of about 600 mg TU. A starting dosage of about 400 mg TU may be advantageous over a starting dosage of about 200 mg TU. Furthermore, providing a Serum Value of testosterone on from about day 1 to about day 21 (e.g., day 1, 2, 3, 4, 5, 6, 7, 8, 9, 10, 11, 12, 13, 14, 15, 16, 17, 18, 19, 20, or 21, e.g., 14) and/or on from about day 35 to about day 49 (e.g., day 35, 36, 37, 38, 39, 40, 41, 42, 43, 44, 45, 46, 47, 48, or 49, e.g., 42) of the treatment regimen may be advantageous over providing a Serum Value of testosterone during days outside of these ranges or particular days. Performing a titration on from about day 1 to about day 35 (e.g., day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, e.g., 28) and/or on from about day 49 to about day 63 (e.g., day 49, 50, 51, 52, 53, 54, 55, 56, 57, 58, 59, 60, 61, 62, or 63, e.g., 56) of the treatment regimen may be advantageous over performing a titration during days outside of these ranges or particular days. Furthermore, using a NaF/EDTA plasma Cavg concentration range of about 400 ng/dL to about 900 mg/dL or a serum Cavg concentration range of about 449 ng/dL to about 1011 ng/dL (e.g., if F is 0.89) or from about 460 ng/dL to about 971 ng/dL (e.g., if the slope 1/F is 1.023 and b is 50.45) to trigger titration decisions may provide a more favorable outcome as compared to a Cavg concentration range of about 300 ng/dL to about 1000 ng/dL. Advantageous properties of using the starting dosages, Cavg boundaries, and days on which to measure a serum or plasma concentration of testosterone and/or perform a titration of the TU dosage described herein include increasing correct titration decisions, decreasing incorrect titration decisions, decreasing the risk of titrations, obtaining a population of subjects in which a greater number of subjects fall within the desired FDA guidelines (e.g., serum Cavg in the normal range of 300 to 1000 ng/dL in 75% of subjects, a Cmax less than 1500 ng/dL in 85% of subjects, not more than 5% between 1800 and 2500 ng/dL, and none above 2500 ng/dL), increasing patient compliance, reducing blood pressure, lowering the risk of increasing blood pressure, and increasing responsivity to the testosterone replacement therapy in order to treat the testosterone deficiency in the subject in need thereof.

EXAMPLES

Example 1. High Dose Titration Scheme

The dose of study drug was titrated during the efficacy period using an algorithm that was developed using 24-hr PK data obtained from the 84-day Phase 2b study of SOV2012-F1 in 36 subjects. The final dose established in the 90-day efficacy period for SOV2012-F1 was used at the start of the 9-month safety evaluation period, and the dose was up- or down-titrated on Days 180 and 270 based on the plasma T concentration from a single blood draw within 3 to 5 hours after dosing (Day 166 and Day 256). Subjects on AndroGel were up- or down-titrated on Day 180 and Day 270 based on single-draw serum T Cpredose levels at Day 166 and Day 256, per product information.

Dose reduction occurred for safety based on hemoglobin levels>18 g/dL nominally measured at Days 90, 180, and 270 during the study.

SOV2012-F1 Group

Dose titration for each subject (starting dose was 400 mg TU a.m. and 200 mg TU p.m.) was based on the plasma T measured between 3 to 5 hours (+10 min) after the morning dose at Day 14 and Day 42. Dose titrations occurred at Day 28 and Day 56, if needed, based on the following algorithm:

For subjects who may need dose titration at Day 28 based on the plasma T level obtained between 3 to 5 hours on Day 14:
T3-5<235 ng/dL: dose increased to 800 mg (400 mg a.m., 400 mg p.m.)
T3-5≥235 to ≤1120 ng/dL: no dose change
T3-5>1120 ng/dL: dose decreased to 400 mg (200 mg a.m., 200 mg p.m.)

For subjects who may need dose titration at Day 56, based on the plasma T level obtained between 3 to 5 hours on Day 42:
For subjects whose dose was not titrated previously (e.g., remained at 400 mg a.m., 200 mg p.m.) and the resulting plasma T3-5 at Day 42 are:
T3-5<235 ng/dL: dose increased to 800 mg (400 mg a.m., 400 mg p.m.)
T3-5≥235 to ≤1120 ng/dL: no dose change
T3-5>1120 ng/dL: dose decreased to 400 mg (200 mg a.m., 200 mg p.m.)

For subjects whose dose was previously decreased to 400 mg (200 mg a.m., 200 mg p.m.), and the resulting plasma T3-5 at Day 42 are:
T3-5<235 ng/dL: dose increased to 600 mg (400 mg a.m., 200 mg p.m.)
T3-5≥235 to ≤1120 ng/dL: no dose change
T3-5>1120 ng/dL: dose may be further decreased to 200 mg a.m.

For subjects whose dose was previously increased to 800 mg (400 mg a.m., 400 mg p.m.), and the resulting plasma T3-5 at Day 42 are:
T3-5<235 ng/dL: The investigator and sponsor will review the data for each individual, and the reason for not responding to the treatment will be further investigated. Assuming correct compliance with the study drug, the dose may be increased to 1000 mg (600 mg a.m., 400 mg p.m.) at the investigator's discretion, taking safety into consideration, or subjects may be discontinued from the study as non-responders.
T3-5≥235 to ≤1120 ng/dL: no dose change
T3-5>1120 ng/dL: dose decreased to 600 mg (400 mg a.m., 200 mg p.m.)

If analysis of the Day 90 24-hour PK data reveals that a subject is on an incorrect dose, discontinuation of the subject may be appropriate.

During the 9-month safety evaluation period, the dose was up- or down-titrated on Days 180 and 270 using a single time point T measurement obtained 3 to 5 hours after the morning dose on Days 166, and 256, respectively. A graphic representation of SOV2012-F1 dose titration in the study is provided in FIG. 1.

Methods

We utilized a similar algorithm from the Axiron product clinical pharmacology review to derive the single blood draw scheme based on data from our Phase IIb trial.

Briefly, we performed comparisons between the titration recommendation made based on the total plasma T concentration (Cx) from a single blood draw and the titration recommendation made based on 24-hour T Cavg or Cmax.

Figure 2:
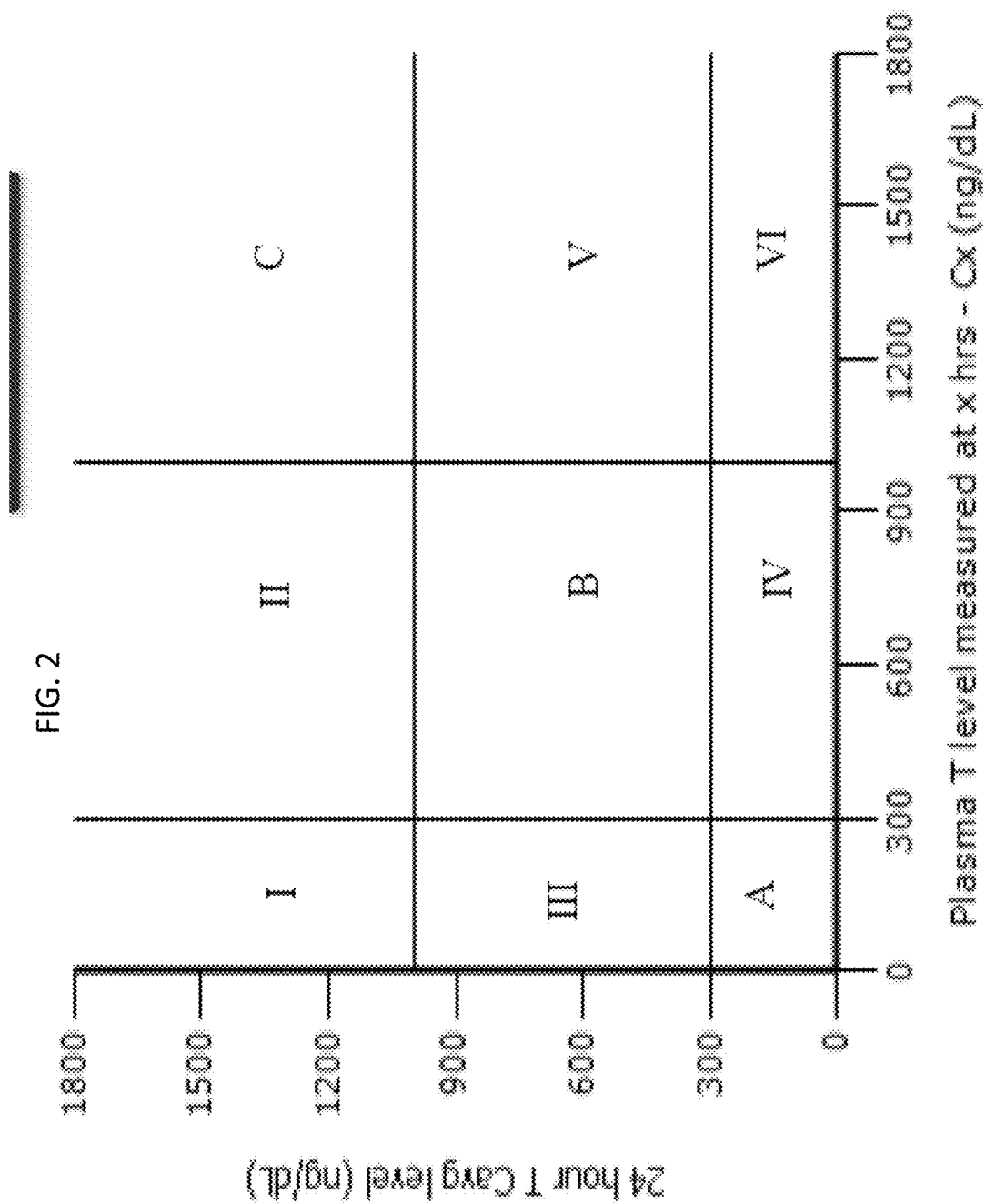
FIG. 2 is a graph illustrating the theoretical outcomes (correct or incorrect) of titration decisions of using a single blood draw at different time points including 0, 1.5, 3, 4, 5, 6, 8, 10, or 12 hr after morning dosing to predict the 24-hour T Cavg as compared to the calculated 24-hour T Cavg. For illustrating the approach, this figure uses the commonly accepted serum normal T-range of 300 to 1000 ng/dL.

FIG. 2 represents the theoretical outcomes (correct or incorrect titration decisions) of using a single blood draw at different time points including 0, 1.5, 3, 4, 5, 6, 8, 10, or 12 hr after morning dosing to predict the 24-hour T Cavg as compared to the calculated 24-hour T Cavg. For illustrating the approach, this figure uses the commonly accepted serum normal T-range of 300 to 1000 ng/dL.

The regions having discrepancies between Cx-based and 24-hour T Cavg-based titration recommendations are defined as "Incorrect" (e.g., regions I-VI), while regions that both titration recommendations agreed are defined as "Correct" (e.g., regions A, B, and C).

The percentage of subjects within A, B, and C regions represent the correct titration decisions made from single blood draw plasma T levels; while percentage of subjects within regions I-VI represent incorrect decisions as described as following:
I: Plasma T level less than 300 ng/dL, but the Cavg greater than 1000 ng/dL
II: Plasma T level in the normal range, but the Cavg greater than 1000 ng/dL
III: Plasma T level less than 300 ng/dL, but the Cavg in the normal range
IV: Plasma T level in the normal range, but the Cavg less than 300 ng/dL
V: Plasma T level greater than 1000 ng/dL, but the Cavg in the normal range
VI: Plasma T level greater than 1000 ng/dL, but the Cavg less than 300 ng/dL In situations described in I, II, and III, the single blood draw based titration recommendation will result in a dose higher than necessary while in situations described in IV, V, and VI, the single blood draw based titration recommendations will result in a dose lower than necessary. The same framework applies to Cmax vs. Cx comparison.

Results

Cavg-Based Decisions

Based on comparisons of 24-hour T Cavg-based titration or Cmax-based titration decisions from Days 7+14 of the Phase 2b study combined (400 mg am/400 mg pm regimen only), we found 0, 1.5, 10 and 12 hours were not suitable for making titration decisions while 3-8 hr post morning dose seemed to be appropriate range for single blood draw.

Figure 3:
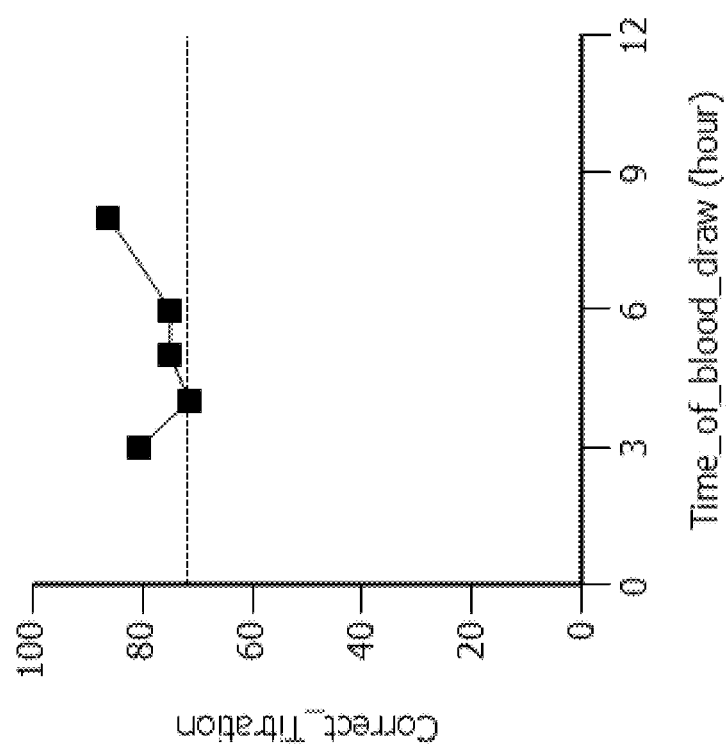
FIG. 3 is a graph showing percentage of subjects at each time point where use of the blood draw would lead to a correct titration decision (Day 7 and 14 based on 24-hour T Cavg).

FIG. 3 suggests that dose titrations based on single blood draws 3-8 hr after morning dosing gave the best match with 24-hour T Cavg-based dose titration recommendations (72-86% correct titration decisions).

Table 1 summarizes the occurrence of each unnecessary titration.

TABLE 1

Potentially Incorrect Dose Decisions by Time of Analysis of Plasma Sample (Day 7 and 14)

| | Time (hr) | | | | |
| --- | --- | --- | --- | --- | --- |
| | 3 | 4 | 5 | 6 | 8 |
| Cx < Cavg: Unnecessary up-titration (%) | 11.1 | 0 | 2.8 | 0 | 13.9 |
| Cx > Cavg: Unnecessary down-titration (%) | 11.1 | 25 | 22.2 | 19.4 | 11.1 |

Figure 4:
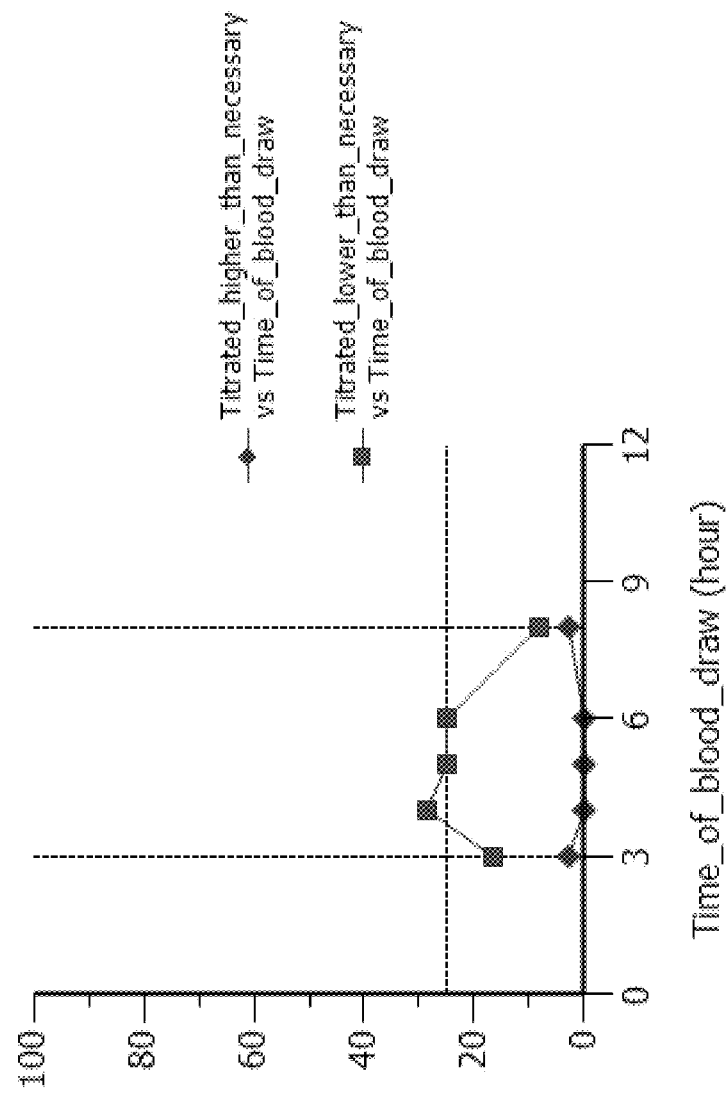
FIG. 4 is a graph illustrating percentage of incorrect titration decisions based on a single blood Draw (Day 7 and 14).

FIG. 4 illustrates the percentage of incorrect titration decisions based on a single blood draw resulting in doses that were higher or lower than necessary. As FIG. 4 suggests, it is reasonable to suggest that subjects should be titrated based on blood draws taken between 3 and 8 hr after morning dose of the drug.

Cmax-Based Decisions in Combination with Cavg

We also compared Cmax based decisions for the impact of different thresholds for down-titration decisions. Incorporation of Cmax into the titration algorithm addresses the safety risk of T levels greater than 1500 ng/dL.

Figure 5:
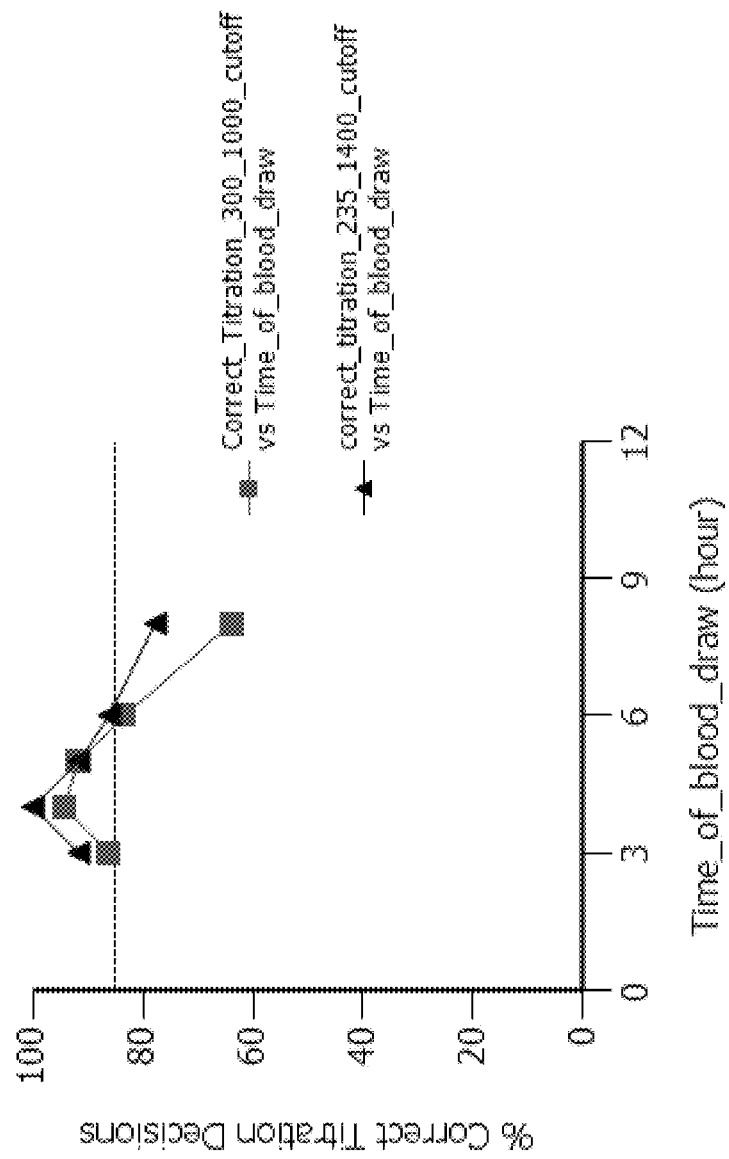
FIG. 5 is a graph showing percentage of subjects at each time point where use of the blood draw would lead to a correct titration decision (Day 7 and 14 based on Cmax 0-12).

FIG. 5 Suggests that dose titrations based on single blood draws between 3 and 5 hr after morning dosing gives the best match with Cmax 0-12 based dose titration recommendations using the thresholds of 235 and 1400 ng/dL (91.7-100%). T-values (Cx) below the lower limit of 235 ng/dL results in up-titration to achieve Cavg within the normal range. T-values (Cx) above the upper limit of 1400 ng/dL result in down-titration to maintain Cmax values less than 1500 ng/dL. Application of the range 300-1000 ng/dL resulted in lower correct titration percentages. Additionally, 8 hrs post morning dosing gives a lower percentage of correct titration decisions, and thus is not recommended. For 6 hr post morning dosing, we observed 5 subjects in the Phase 2b study having Cmax over 1600 ng/dL but not meeting down-titration decisions based on plasma T level. Therefore, we propose to use the window of 3-5 hr for our Phase 3 trial.

TABLE 2

Potentially Incorrect Dose Decisions by Time of Analysis of Plasma Sample (Day 7 and 14 data from Phase 2b study).

| | Time (hr) | | | | |
|---|---|---|---|---|---|
| | 3 | 4 | 5 | 6 | 8 |
| Cut-off: 300-1000 ng/dL: | | | | | |
| Cx < Cavg: Unnecessary up-titration (%) | 11.1 | 0 | 2.8 | 8.3 | 27.8 |
| Cx > Cavg: Unnecessary down-titration (%) | 2.8 | 5.6 | 5.6 | 8.3 | 8.3 |
| Cut-off: 235-1400 ng/dL: | | | | | |
| Cx < Cavg: Unnecessary up-titration (%) | 8.3 | 0 | 8.3 | 13.9 | 22.2 |
| Cx > Cavg: Unnecessary down-titration (%) | 0 | 0 | 0 | 0 | 0 |

Table 2 confirmed that 6 and 8 hr are not appropriate for single blood draw, and the window of 235-1400 ng/dL provided lower incorrect percentages for both cases.

It was proposed to use 3-5 hr post morning dose as the single blood draw time window. The up- and down-titration thresholds are set at 235 ng/dL and 1400 ng/dL, respectively to achieve a high percentage of correct decision while minimizing the percentage of incorrect decisions.

Both Days 49 and 84 in the Phase IIb trial have 24-hour PK data. We evaluated data for these two days on 15 subjects who received 400 mg A.M./200 mg P.M. dose regimen, which is the starting dose in the Phase 3 trial. The proposed titration window of 3-5 hr single blood draw and 235-1400 ng/dL threshold values were validated by this approach.

Titration Scheme

In conclusion, we propose that the single blood draw used for titration decisions be obtained 3-5 hr post morning dose. Subjects having single blood draw values of total plasma T less than or equal to 235 ng/dL were up-titrated. Subjects having single blood draw values of total plasma T greater than 1120 ng/dL were down-titrated.

Example 2. Adjustment of New Dosing Titration Scheme

Number of Subjects

Up to approximately 170 completed subjects consented to the Study 1 EXT Study to undergo 8 weeks or more of washout from study medication or interim testosterone replacement therapy, followed by a total of 180 days of treatment with SOV2012-F1. Subjects were dose-titrated to their final dose over the first 28-56 days of the treatment period. The Study 1 EXT Study included three to four 24-hour ABPM assessment sessions, depending on at which timepoint the subject entered the study (directly from Study 1 or as a Late Entry Subject to Study 1 EXT or as a newly enrolled Study 1-naïve subject).

Approximately 135 of the approximately 170 consented subjects (80%) were targeted to complete 120 days of the 180-day treatment period, including at minimum, the baseline Day 1 and the 4-month Day 120 required 24-hr ABPM assessment sessions in Study 1 EXT.

Treatment During Extension Study, Study 1 EXT

During the Study 1 EXT study period, all subjects were washed out from their originally assigned Study 1 study medication or any interim testosterone replacement for an 8-week period. At the completion of that washout, all subjects received SOV2012-F1, starting at a total daily dose of 400 mg (200 mg with the breakfast meal and 200 mg with the dinner meal) and were titrated, if needed, according to the dose titration algorithm established for the Study 1 EXT protocol. Dietary guidance and meal content were unchanged from Study 1 protocol.

Extension Study Duration

Primary Endpoint

Change from baseline in 24-hour average ambulatory systolic blood pressure after approximately 120 days (±3) of treatment.

To determine the response to a lower starting dose of oral SOV2012-F1 with up and down titration as appropriate, as measured by:

Percentage of SOV2012-F1-treated subjects with a plasma T Cavg within the normal range after 90 days of treatment.

Secondary Endpoints

Change from baseline in 24-hour average ambulatory systolic blood pressure after approximately 180 days (±3) of treatment.

Change from baseline in 7 AM to 10:30 PM—hour average ambulatory systolic blood pressure (daytime) after approximately 120 days (±3) and 180 days (±3) of treatment.

Change from baseline in 11 PM to 6:30 AM—hour average ambulatory systolic blood pressure (nighttime) after approximately 120 days (±3) and 180 days (±3) of treatment.

Maximum 24-hour systolic blood pressure after approximately 120 days (±3) and 180 days (±3) of treatment.

Change from baseline in 7 AM to 10:30 PM—hour average ambulatory diastolic blood pressure (daytime) after approximately 120 days (±3) and 180 days (±3) of treatment.

Change from baseline in 11 PM to 6:30 AM—hour average ambulatory diastolic blood pressure (nighttime) after approximately 120 days (±3) and 180 days (±3) of treatment.

Change from baseline in 24-hour mean diastolic blood pressure (dBP) measured by ABPM after 120 (±3) days and 180 (±3) days of treatment, in SOV2012-F1-treated subjects.

Maximum 24-hour diastolic blood pressure after approximately 120 days (±3) and 180 days (±3) of treatment.

Change from baseline in 24-hour average ambulatory heartrate after approximately 120 days (±3) and 180 days (±3) of treatment.

Change from baseline in 7 AM to 10:30 PM—hour average ambulatory heartrate (daytime) after approximately 120 days (±3) and 180 days (±3) of treatment.

Change from baseline in 11 PM to 6:30 AM—hour average ambulatory heartrate (nighttime) after approximately 120 days (±3) and 180 days (±3) of treatment.

Observed and change from baseline in half hourly systolic blood pressure, diastolic blood pressure, and heartrate after approximately 120 days (±3) and 180 days (±3) of treatment.

The percentage of SOV2012-F1-treated subjects with maximum plasma testosterone concentration (T Cmax) values after 90 days of treatment:
<1500 ng/dL;
>1800 to 2500 ng/dL;
>2500 ng/dL.

Safety Endpoints

To determine the incidence of AEs, SAEs, and AEs leading to Study 1 EXT withdrawal in SOV2012-F1-treated subjects.

Observed and change from baseline in BP and HR obtained in-clinic during the treatment period.

Observed and change from baseline in the following laboratory parameters in SOV2012-F1-treated subjects during the treatment period:

Liver function tests (alanine aminotransferase [ALT], aspartate aminotransferase [AST], total bilirubin, alkaline phosphatase)

Hematology parameters (hemoglobin)

Hormone levels (luteinizing hormone [LH], follicle-stimulating hormone [FSH], DHT, sex hormone-binding globulin [SHBG], and thyroid-stimulating hormone [TSH])

Lipid profiles (high-density lipoproteins, low-density lipoproteins, total cholesterol, and triglycerides)

Serum PSA

SOV2012-F1 Dose Titration

The dose of study drug was titrated during the efficacy period using an algorithm that was developed using 90-day 24-hr PK data obtained from 133 Study 1 subjects in the SOV2012-F1 treatment group. Dose titration for each subject was based on the NaF/EDTA plasma T measured between 3 to 5 hours (+10 min) after the morning dose at Day 14 and Day 42. Dose titrations occurred at Day 28 and Day 56 if needed, based on the following algorithm:

For subjects who may need dose titration at Day 28 based on the plasma T level obtained between 3 to 5 hours on Day 14:
T3-5<400 ng/dL: dose increased to 600 mg (300 mg AM, 300 mg PM)
T3-5≥400 to ≤900 ng/dL: no dose change
T3-5>900 ng/dL: dose decreased to 200 mg (100 mg AM, 100 mg PM)

For subjects who may need dose titration at Day 56, based on the plasma T level obtained between 3 to 5 hours on Day 42:

For subjects whose dose was not titrated previously (e.g., remained at 200 mg AM, 200 mg PM) and the resulting plasma T3-5 at Day 42 are:
T3-5<400 ng/dL: dose increased to 600 mg (300 mg AM, 300 mg PM)
T3-5≥400 to ≤900 ng/dL: no dose change
T3-5>900 ng/dL: dose decreased to 200 mg (100 mg AM, 100 mg PM)

For subjects whose dose was previously decreased to 200 mg (100 mg AM, 100 mg p.m.), and the resulting plasma T3-5 at Day 42 are:
T3-5<400 ng/dL: dose increased to 400 mg (200 mg AM, 200 mg PM)
T3-5≥400 to 900 ng/dL: no dose change
T3-5>900 ng/dL: dose decreased to 100 mg AM only.

For subjects whose dose was previously increased to 600 mg (300 mg AM, 300 mg PM), and the resulting plasma T3-5 at Day 42 are:
T3-5<400 ng/dL: dose increased to 800 mg (400 mg AM, 400 mg PM)
T3-5≥400 to ≤900 ng/dL: no dose change
T3-5>900 ng/dL: dose decreased to 400 mg (200 mg AM, 200 mg PM)

Measuring T at 3 to 6 Hours

Figure 7:
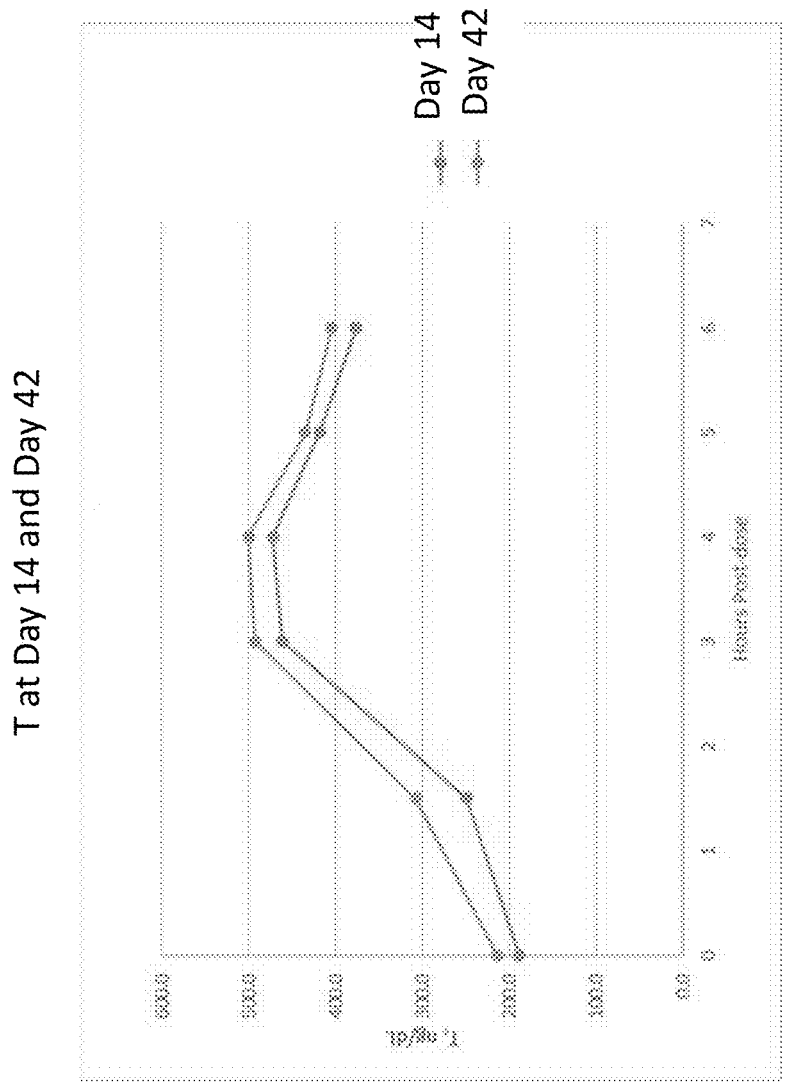
FIG. 7 is a graph showing the mean plasma T concentration from 0 to 6 hours post dose on day 14 and day 42.
Figure 8:
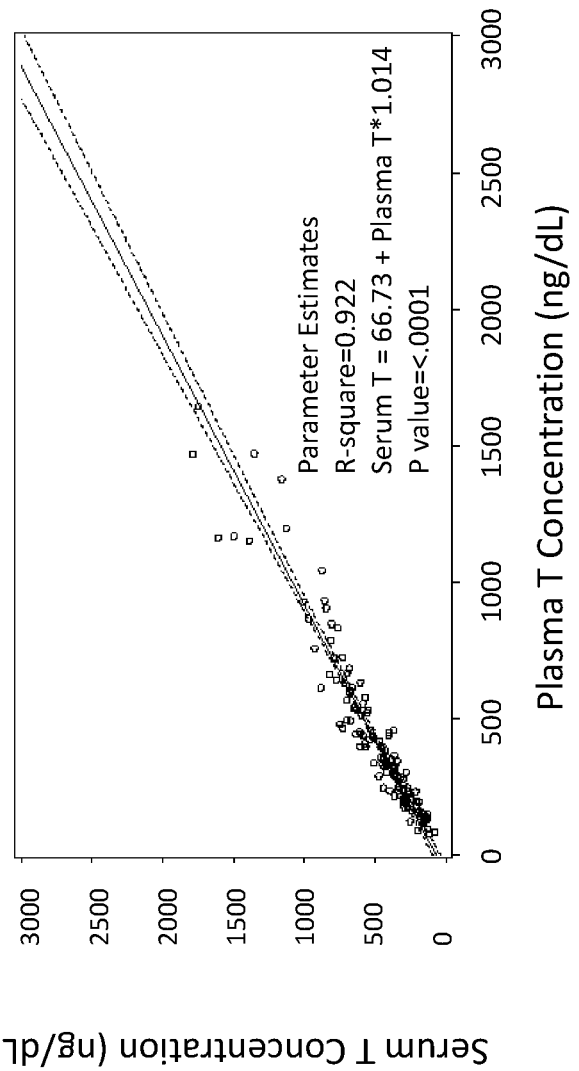
FIG. 8 is a regression plot of serum versus plasma concentrations using serum-plasma concentration pairs obtained between 3 and 5 hours after morning dose.

In the Study 1 EXT, it was identified that measuring plasma T concentration at from about 3 hours to about 6 hours after administration provided a reliable plasma concentration for the phytosterol ester-containing formulation administered with a meal. The T concentration over the period 0 to 6 hours post-dose for Visits on Days 14 and 42 of the Study 1 EXT. The T measurements were made using plasma samples collected with NaF/EDTA tubes and analyzed by LC-MS/MS. FIG. 7 shows a low T level from hours 0 to 2 post-dose and a relatively flat PK curve from hours 3 to 6 post-dose, illustrating the constant plasma T value in this window.

The ratio of plasma to serum results over the 3 to 6 hour window were also consistent. If the ratio changed significantly over the window, then the titration thresholds above would be time-dependent. Table 3 below shows that predetermined factor F varies within a narrow range, thereby allowing the adjustment of dose based on samples obtained in the 3 to 6 hour window.

TABLE 3

Predetermined factor F in post-dose window

| Plasma/Serum Ratio | Post-Dose Timepoint, hrs | | | |
|---|---|---|---|---|
| | 3 | 4 | 5 | 6 |
| Day 14 | 0.87 | 0.88 | 0.85 | 0.83 |
| Day 42 | 0.92 | 0.92 | 0.90 | 0.92 |
| Days 14 and 42 Mean over 3, 4 and 5 hours | | 0.89 | | — |
| Days 14 and 42 Mean over 3, 4, 5 and 6 hours | | | 0.89 | |

Efficacy (Cavg)

The primary efficacy endpoint was the percentage of SOV2012-F1-treated subjects with a 24-hour total T Cavg within the normal range after 90 days of treatment within the extension.

The Cavg was calculated as area under the concentration-time curve from time 0 to 24 hours (AUC0-24) divided by the actual number of hours between dosing and the 24-hour sample collection time.

Ambulatory Systolic Blood Pressure (sBP)

The change from baseline in the 24-hour average sBP was analyzed as the primary blood pressure endpoint. Key secondary analyses were derived from the changes from baseline in the daytime and night time sBP.

The difference in least squares means and associated 90% CI were provided.

Ambulatory Diastolic Blood Pressure (dBP) and Ambulatory Heartrate (HR)

These were evaluated in a similar fashion to the sBP except for the maximum heartrate. Hourly and half hourly observed and time matched change from baseline were descriptively summarized.

Cmax

The secondary endpoint was evaluated by estimating the proportion of SOV2012-F1 treated subjects Day 90 with T Cmax:

a) T Cmax≤1500 ng/dL
b) T Cmax>1800 and 2500 ng/dL
c) T Cmax>2500 ng/dL

Titration Decisions

Using the T concentrations obtained at the titration timepoints with EDTA and serum tubes, exploratory analysis was performed to compare the predicted titration decisions with those which were made using NaF-EDTA samples. Table 4 shows the dose distribution of subjects from the Study 1 and Study 1 EXT at Day 90.

TABLE 4

Non-final data at Day 90 of each study.

| | Study: daily dose | | | | | |
|---|---|---|---|---|---|---|
| | 100 mg | 200 mg | 400 mg | 600 mg | 800 mg | 1000 mg |
| Study 1 (n = 187) | Dose not used | 3% | 28% | 61% | 7% | 1% |
| Study 1 EXT (n = 146) | 2% | 6% | 23% | 44% | 25% | Dose not used |

In summary, there were subjects in Study 1 EXT who were started at 400 mg daily of SOV2012-F1 and had plasma T measurements obtained in the window of 3 to 5 hours post-morning dose, and who had no dose adjustments against titration thresholds of 400 and 900 ng/dl (plasma NAF/EDTA). These subjects had the surprising results of both Cavg in the normal range, Cmax values conforming to the FDA criteria, and blood pressure results of less than 3.8 mm increase (e.g. less than 2 mm increase, less than 3 mm increase). Heart rate increases were also superior (less increase versus baseline).

Figure 6:
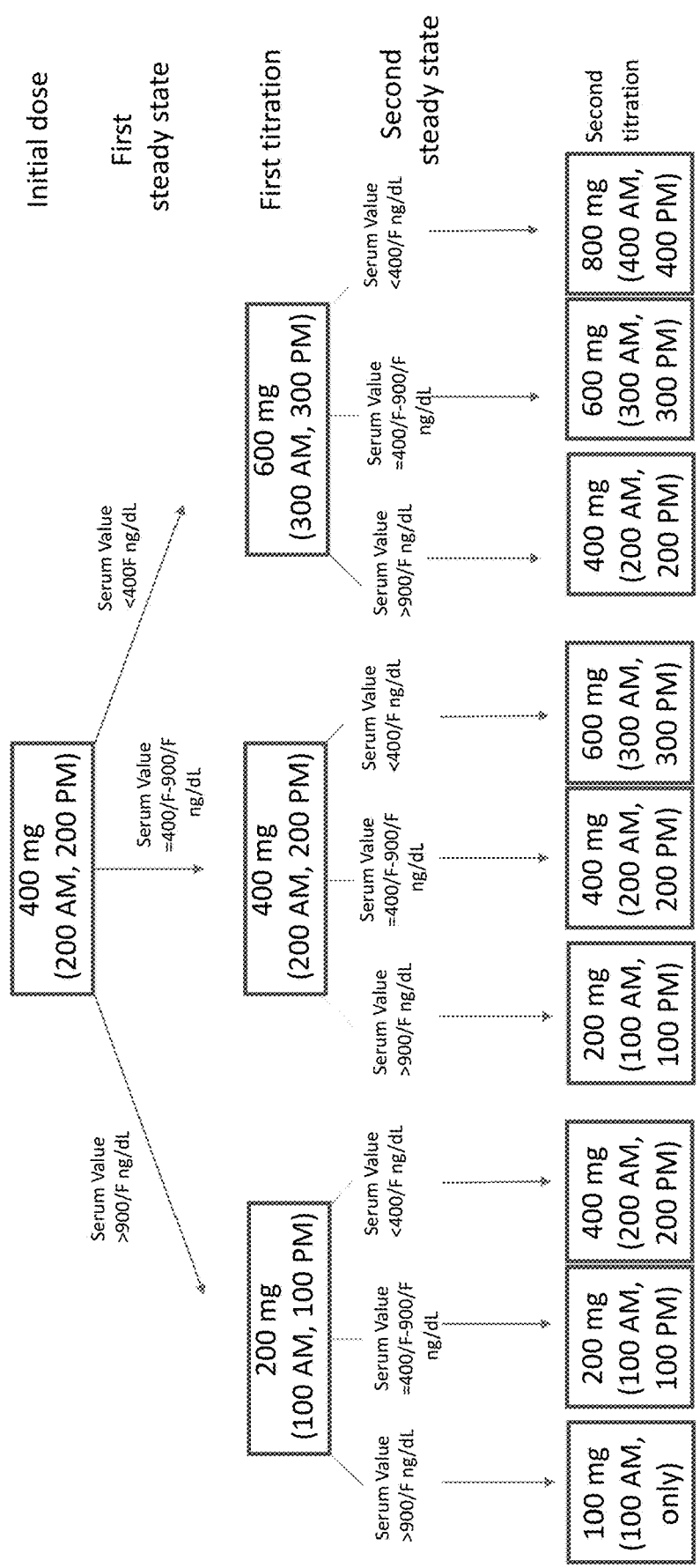
FIG. 6 is a schematic flow chart showing a titration algorithm as described herein.

Additionally, we identified subjects who were started at 400 mg daily of SOV2012-F1, had plasma T measurements obtained in the window of 3 to 5 hours (or 3 to 6 hours) post-morning dose, and who had dose titrations against 400 and 900 ng/dL plasma (NaF/EDTA) thresholds (FIG. 6). These subjects had the surprising results of both Cavg in the normal range, Cmax values conforming to the FDA criteria, and blood pressure results of less than 4.9 mm increase (e.g. less than 2 mm increase, less than 3 mm increase). These blood pressure measurements were made by the ABPM protocol. Heart rate increases were also superior (less increase versus baseline).

Example 3. Blood Pressure is Minimally Affected With This Titration Scheme

Ambulatory blood pressure measurements were obtained for 134 subjects as described above in Example 2. These data were directly compared to a TU formulation from Clarus Therapeutics that lacks phytosterol esters and was not subject to the same dosing titration regimen described herein. Table 5 below illustrates the results.

TABLE 5

Changes from baseline in blood pressure parameters in ABPM patients in study CLAR-15012 (TU) and Study 1 EXT (SOV2012-F1)

| Increases | ALL ABPM patients | |
|---|---|---|
| Decreases (LS means) | CLAR (N = 135) | SOV2012-F1 (N = 134) |
| 24 hr heart rate HR* (bpm) | +2.2 | +0.71 |
| Daytime systolic BP (mmHg) | +5.0 | +1.70 |
| Nighttime systolic BP (mmHg) | +4.9 | +1.65 |
| 24 hr average systolic BP (mmHg) | +4.9 | +1.64 |

*24 hour average heart rate in beats per minute,
LS = least squared means

These data show that ABPM measurements for all patients increased by only 1.70 mmHg during the daytime, 1.65 mmHg during the nighttime, and 1.64 mmHg over a 24-hour average, relative to baseline, as compared to 5.0 mmHg, 4.9 mmHg, and 4.9 mmHg, respectively, for patients undergoing treatment with the Clarus formulation.

Furthermore, in-clinic systolic blood pressure and heart rate data for the Study 1 and Study 1 EXT are provided below. As is shown in Tables 6 and 7 below, the Study 1 EXT produced a slower rise and lower maximum systolic blood pressure measurements than the Study 1 protocol. The average change from baseline for heartrate from the $90^{th}$ day to the $180^{th}$ day for the Study 1 EXT was 2.2 beats per minute (bpm), and the average change of the Study 1 (Days 90 and 180) was 3.3 bpm change from baseline.

TABLE 6

Study 1 and Study 1 EXT Heart Rate Data

| | Study 1 SOV2012-F1 (N = 214) | Study 1 EXT SOV2012-F1 (N = 106) |
|---|---|---|
| Baseline | | |
| n | 214 | 104 |
| Mean(SE) | 69.93 (0.573) | 70.95 (0.927) |
| 95 CI | 68.80, 71.06 | 69.11, 72.79 |
| Day 14 | | |
| n | 205 | 99 |
| Mean(SE) | 2.71 (0.518) | 0.93 (0.784) |
| 95 CI | 1.69, 3.74 | −0.63, 2.49 |
| Day 42 | | |
| n | 197 | 98 |
| Mean(SE) | 3.84 (0.641) | 1.69 (0.939) |
| 95 CI | 2.57, 5.10 | −0.17, 3.56 |
| Day 90 | | |
| n | 187 | 98 |
| Mean(SE) | 4.34 (0.610) | 2.12 (0.920) |
| 95 CI | 3.14, 5.55 | 0.30, 3.95 |
| Day 119 | | |
| n | NA | 93 |
| Mean(SE) | NA | 1.24 (0.919) |
| 95 CI | NA | −0.59, 3.06 |
| Day 180 | | |
| n | 176 | 64 |
| Mean(SE) | 2.26 (0.641) | 3.14 (1.253) |
| 95 CI | 1.00, 3.53 | 0.64, 5.64 |

TABLE 8

Study 1 and Study 1 EXT Systolic Blood Pressure Data

|  | Study 1<br>SOV2012-F1<br>(N = 214) | Study 1 EXT<br>SOV2012-F1<br>(N = 106) |
|---|---|---|
| Baseline | | |
| n | 214 | 104 |
| Mean(SE) | 125.99 (0.618) | 125.64 (0.986) |
| 95 CI | 124.77, 127.21 | 123.69, 127.60 |
| Day 14 | | |
| n | 205 | 99 |
| Mean(SE) | 0.92 (0.628) | 1.07 (1.030) |
| 95 CI | −0.31, 2.16 | −0.97, 3.12 |
| Day 42 | | |
| n | 197 | 98 |
| Mean(SE) | 2.59 (0.749) | 1.05 (0.946) |
| 95 CI | 1.11, 4.06 | −0.83, 2.93 |
| Day 90 | | |
| n | 187 | 98 |
| Mean(SE) | 2.05 (0.756) | 2.30 (1.039) |
| 95 CI | 0.56, 3.54 | 0.23, 4.36 |
| Day 119 | | |
| n | NA | 93 |
| Mean(SE) | NA | 3.44 (1.035) |
| 95 CI | NA | 1.39, 5.50 |
| Day 180 | | |
| n | 176 | 64 |
| Mean(SE) | 2.19 (0.795) | 3.23 (1.091) |
| 95 CI | 0.62, 3.76 | 1.06, 5.41 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of treating testosterone deficiency in a subject in need thereof, the method comprising:
   a) performing a treatment regimen comprising orally administering to the subject 400 mg of testosterone undecanoate (TU) daily with a meal, wherein the TU is administered in a pharmaceutical composition comprising TU, a non-sterol solubilizing agent effective for solubilization of the TU, and a phytosterol or phytosterol ester;
   b) establishing a first steady state serum concentration of testosterone;
   c) following step (b), providing a first steady state Serum Value of testosterone in the subject that is measured from about 3 hours to about 6 hours after administration of the pharmaceutical composition; and
   d) performing a first titration of the testosterone undecanoate, wherein:
      i) if the first Serum Value of testosterone is less than about 460 ng/dl, then orally administering to the subject about 600 mg TU daily to establish a second steady state Serum Value of testosterone that is higher than the first steady state Serum Value of testosterone;
      ii) if the first Serum Value of testosterone is from about 460 ng/dl to about 971 ng/dl, then continuing to orally administer to the subject about 400 mg TU daily to maintain the first steady state Serum Value of testosterone; or
      iii) if the first Serum Value of testosterone is greater than about 971 ng/dl, then orally administering to the subject about 200 mg TU daily to establish a second steady state Serum Value of testosterone that is lower than the first steady state Serum Value of testosterone.

2. The method of claim 1, wherein step (a) comprises administering the pharmaceutical composition twice daily.

3. The method of claim 2, wherein:
   a) a first dose is administered in the morning and a second dose is administered in the evening; and/or
   b) the first dose comprises about 200 mg TU, and the second dose comprises about 200 mg TU.

4. The method of claim 3, wherein following the first titration,
   i) about 600 mg TU is administered daily to the subject, and the first dose comprises about 300 mg TU, and the second dose comprises about 300 mg TU;
   ii) about 400 mg TU is administered daily to the subject, and the first dose comprises about 200 mg TU, and the second dose comprises about 200 mg TU; or
   iii) about 200 mg TU is administered daily to the subject, and the first dose comprises about 100 mg TU, and the second dose comprises about 100 mg TU.

5. The method of claim 1, further comprising:
   e) establishing a second steady state serum concentration of testosterone;
   f) following step (e), providing a second steady state Serum Value of testosterone in the subject; and
   g) performing a second titration of the TU.

6. The method of claim 5, wherein following the first titration, about 600 mg TU is administered daily to the subject, and
   a) if the second Serum Value of testosterone is less than about 460 ng/dL, then orally administering about 800 mg TU daily to the subject to establish a third steady state Serum Value of testosterone that is higher than the second steady state Serum Value of testosterone;
   b) if the second Serum Value of testosterone is from about 460 ng/dL to about 971 ng/dL, then continuing to orally administer about 600 mg TU daily to the subject to maintain the second steady state Serum Value of testosterone; or
   c) if the second Serum Value of testosterone is greater than about 971 ng/dL, then orally administering about 400 mg TU daily to the subject to establish a third steady state Serum Value of testosterone that is lower than the second steady state Serum Value of testosterone.

7. The method of claim 5, wherein following the first titration, about 400 mg TU is administered daily to the subject, and
   a) if the second Serum Value of testosterone is less than about 460 ng/dL, then orally administering about 600 mg TU daily to the subject to establish a third steady state Serum Value of testosterone that is higher than the second steady state Serum Value of testosterone;
   b) if the second Serum Value of testosterone is from about 460 ng/dL, then continuing to orally administer about 400 mg TU daily to the subject to maintain the second steady state Serum Value of testosterone; or
c) if the second Serum Value of testosterone is greater than about 971 ng/dL, orally administering about 200 mg TU daily to the subject to establish a third steady state Serum Value of testosterone that is lower than the second steady state Serum Value of testosterone.

8. The method of claim 7, wherein following the first titration, about 200 mg TU is administered daily to the subject, and
a) if the second Serum Value of testosterone is less than about 460 ng/dL, orally administering about 400 mg TU daily to the subject to establish a third steady state Serum Value of testosterone that is higher than the second steady state Serum Value of testosterone;
b) if the second Serum Value of testosterone is from about 460 ng/dL to about 971 ng/dL, then continuing to orally administer about 200 mg TU daily to the subject to maintain the second steady state Serum Value of testosterone; or
c) if the second Serum Value of testosterone is greater than about 971 ng/dL, orally administering about 100 mg TU daily to the subject to establish a third steady state Serum Value of testosterone that is lower than the second steady state Serum Value of testosterone.

9. The method of claim 6, wherein following the second titration, about 800 mg TU is administered daily to the subject, and the first dose comprises about 400 mg TU, and the second dose comprises about 400 mg TU.

10. The method of claim 7, wherein following the second titration, about 100 mg TU is administered daily to the subject, and the subject receives a single dose of about 100 mg TU.

11. The method of claim 1, wherein:
a) the first Serum Value of testosterone is measured prior to day 21 of the treatment regimen; and/or
b) the first titration is performed on from about day 7 to about day 35 of the treatment regimen.

12. The method of claim 11, wherein:
a) the first Serum Value of testosterone is measured on about day 7 of the treatment regimen; and/or
b) the first titration is performed on about day 28 of the treatment regimen.

13. The method of claim 1, wherein the pharmaceutical composition comprises:
a) from about 10% to about 25% by weight of solubilized testosterone undecanoate;
b) from about 5% to about 40% by weight of a hydrophilic surfactant;
c) from about 15% to about 65% by weight of a hydrophobic surfactant;
d) from about 2% to about 45% by weight of phytosterol esters; and
e) from about 0% to about 15% by weight of a solubilizer.

14. The method of claim 13, wherein the pharmaceutical composition comprises:
a) about 18.2% by weight of solubilized testosterone undecanoate;
b) about 15.0% by weight of polyoxyl 40 hydrogenated castor oil;
c) about 39.9% by weight of propylene glycol monolaurate;
d) about 25.0% by weight of one or more phytosterol esters; and
e) about 2.0% by weight of di-alpha-tocopherol and/or an ester or acetate thereof.

15. The method of claim 1, wherein:
a) the subject is a hypogonadal male;
b) the subject has not previously been administered TU or other testosterone replacement therapy for a period of at least seven days or a period of time sufficient to completely wash exogenous testosterone from the subject; and/or
c) the method is performed on a population of human subjects.

16. The method of claim 15, wherein:
a) the population comprises at least 10 subjects, at least 50 subjects, at least 100 subjects, at least 200 subjects, at least 500 subjects, or more;
b) the method achieves a Cavg in the serum normal range of about 300 ng/dL to about 1000 ng/dL in at least 75% of the population;
c) the method achieves a Cmax of less than about 1500 ng/dL in at least 85% of the population;
d) the method achieves a Cmax of from about 1800 ng/dL to about 2500 ng/dL in no more than 5% of the population;
e) the method achieves a Cmax of greater than about 2500 ng/dL in no more than 0% of the population;
f) the method reduces an average number of incorrect titrations or the risk of incorrect titrations per subject in the population in order to achieve a steady state testosterone Serum Value of from about 300 ng/dL to about 1000 ng/dl relative to a population receiving a treatment regimen in which an initial dosage is not about 400 mg TU and/or the Serum Value is not measured from about 3 hours to about 6 hours after administration
g) the method achieves a Cavg in the serum normal range of about 300 ng/dl to about 1000 ng/dL in a greater number of subjects in the population as compared to a treatment regimen in which an initial dosage is not about 400 mg TU and/or the Serum Value is not measured from about 3 hours to about 6 hours after administration;
h) the method achieves a Cmax of less than about 1500 ng/dL in a greater number of subjects in the population as compared to the treatment regimen in which the initial dosage is not about 400 mg TU and/or the Serum Value is not measured from about 3 hours to about 6 hours after administration;
i) The method achieves a Cmax of from about 1800 ng/dL to about 2500 ng/dL in a fewer number of subjects in the population as compared to the treatment regimen in which the initial dosage is not about 400 mg TU and/or the Serum Value is not measured from about 3 hours to about 6 hours after administration;
j) the method achieves a Cmax of greater than about 2500 ng/dL in a fewer number of subjects in the population as compared to the treatment regimen in which the initial dosage is not about 400 mg TU and/or the Serum Value is not measured from about 3 hours to about 6 hours after administration; and/or
k) the method decreases the risk of elevated blood pressure of the population of human subjects.

17. The method of claim 16, wherein the daytime systolic blood pressure, night time systolic blood pressure, and/or 24-hour average systolic blood pressure does not increase by more than 3 mmHg as compared to the blood pressure before onset of treatment in the population of human subjects.

18. The method of claim 1, wherein the first Serum Value is measured by:
   measuring testosterone concentration of serum clotted at room temperature for about 30 minutes prior to centrifugation in a tube.

19. The method of claim 5, wherein the second Serum Value is measured by:
   measuring testosterone concentration of serum clotted at room temperature for about 30 minutes prior to centrifugation in a tube.

20. The method of claim 1, wherein the first steady state Serum Value of testosterone in the subject is measured from about 3 hours to about 5 hours after administration of the pharmaceutical composition.

21. The method of claim 1, wherein the second steady state Serum Value of testosterone in the subject is measured from about 3 hours to about 5 hours after administration of the pharmaceutical composition.

* * * * *